(12) United States Patent
Pentelute et al.

(10) Patent No.: US 12,370,261 B2
(45) Date of Patent: Jul. 29, 2025

(54) CHIMERIC PEPTIDES FOR ANTISENSE DELIVERY

(71) Applicants: Sarepta Therapeutics, Inc., Cambridge, MA (US); Massachusetts Institute of Technology, Cambridge, MA (US)

(72) Inventors: Bradley L. Pentelute, Cambridge, MA (US); Colin M. Fadzen, Cambridge, MA (US); Rebecca L. Holden, Cambridge, MA (US); Justin M. Wolfe, Cambridge, MA (US); Zi-Ning Choo, Cambridge, MA (US); Monica Yao, Cambridge, MA (US); Gunnar J. Hanson, Cambridge, MA (US)

(73) Assignees: Sarepta Therapeutics, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 154 days.

(21) Appl. No.: 16/981,145

(22) PCT Filed: Mar. 15, 2019

(86) PCT No.: PCT/US2019/022475
§ 371 (c)(1),
(2) Date: Sep. 15, 2020

(87) PCT Pub. No.: WO2019/178479
PCT Pub. Date: Sep. 19, 2019

(65) Prior Publication Data
US 2021/0260206 A1    Aug. 26, 2021

Related U.S. Application Data

(60) Provisional application No. 62/644,202, filed on Mar. 16, 2018.

(51) Int. Cl.
*A61K 47/00* (2006.01)
*A61K 47/54* (2017.01)
*A61K 47/64* (2017.01)
*C12N 15/113* (2010.01)

(52) U.S. Cl.
CPC ........ *A61K 47/6455* (2017.08); *A61K 47/545* (2017.08); *C12N 15/113* (2013.01); *C12N 2310/11* (2013.01); *C12N 2310/314* (2013.01); *C12N 2310/3233* (2013.01); *C12N 2310/3513* (2013.01)

(58) Field of Classification Search
CPC ............. A61K 47/6455; A61K 47/545; A61K 47/645; A61K 47/64; C12N 15/113; C12N 2310/11; C12N 2310/314; C12N 2310/3233; C12N 2310/3513
See application file for complete search history.

(56) References Cited

U.S. PATENT DOCUMENTS

| | | | |
|---|---|---|---|
| 2009/0088562 A1 | 4/2009 | Weller et al. | |
| 2014/0315862 A1 | 10/2014 | Kaye | |
| 2015/0080311 A1 | 3/2015 | Moulton et al. | |
| 2015/0211021 A1* | 7/2015 | de Mollerat du Jeu | C12N 15/88 |
| | | | 435/320.1 |
| 2015/0238627 A1 | 8/2015 | Leger et al. | |
| 2017/0165290 A1 | 6/2017 | Dong et al. | |
| 2021/0290772 A1* | 9/2021 | Wolfe | A61K 47/6455 |

FOREIGN PATENT DOCUMENTS

| | | |
|---|---|---|
| CN | 103619356 B | 9/2017 |
| JP | 2003533986 A | 11/2003 |
| JP | 2008513012 A | 5/2008 |
| JP | 2015504650 A | 2/2015 |
| JP | 2016521119 A | 7/2016 |
| WO | WO-2007009094 A2 | 1/2007 |

(Continued)

OTHER PUBLICATIONS

Extended European Search Report for European Application No. 19767585.3, mailed Dec. 23, 2021, 9 pages.
International Preliminary Report on Patentability for International Application No. PCT/US2019/022475, mailed Sep. 22, 2020, 7 pages.
International Search Report for International Application No. PCT/US2019/022475, mailed May 23, 2019, 5 pages.
Saleh et al., "Synthesis and Splice-Redirecting Activity of Branched, Arginine-Rich Peptide Dendrimer Conjugates of Peptide Nucleic Acid Oligonucleotides", Bioconjugate Chemistry 21(10):1902-1911 (2010).

(Continued)

Primary Examiner — Jeanette M Lieb
(74) Attorney, Agent, or Firm — Sterne, Kessler, Goldstein & Fox P.L.L.C.

(57) ABSTRACT

Provided herein are oligonucleotides, chimeric peptides, and peptide-oligonucleotide-conjugates, the chimeric peptides and peptide-oligonucleotide-conjugates comprising at least two cell-penetrating peptides, wherein at least one of the cell-penetrating peptides is an amphipathic peptide and at least one of the cell-penetrating peptides is an oligoarginine peptide. The oligoarginine peptide comprises the sequence $[(RY_zR)_x]$ (SEQ ID NOs: 15-18), wherein R is arginine, Y is independently selected from aminohexanoic acid (X) or β-alanine (B). Also provided herein are methods of treating a muscle disease, a viral infection, or a bacterial infection in a subject in need thereof, comprising administering to the subject oligonucleotides, chimeric peptides, and peptide-oligonucleotide-conjugates comprising at least two cell-penetrating peptides, wherein at least one of the cell-penetrating peptides is an amphipathic peptide and at least one of the cell-penetrating peptides is an oligoarginine peptide described herein.

19 Claims, 6 Drawing Sheets
Specification includes a Sequence Listing.

(56) References Cited

FOREIGN PATENT DOCUMENTS

| WO | WO 2008/036127 A2 | 3/2008 |
| WO | WO 2009/147368 A1 | 12/2009 |
| WO | WO 2012/150960 A1 | 11/2012 |
| WO | WO 2013/017631 A1 | 2/2013 |
| WO | WO 2014/124952 A1 | 8/2014 |
| WO | WO 2015/038933 A1 | 3/2015 |
| WO | WO 2016/087842 A1 | 6/2016 |
| WO | WO 2017/066789 A1 | 4/2017 |
| WO | WO 2019/079386 A1 | 4/2019 |

OTHER PUBLICATIONS

Yin et al., "Context Dependent Effects of Chimeric Peptide Morpholino Conjugates Contribute to Dystrophin Exon-skipping Efficiency", *Molecular Therapy—Nucleic Acids* vol. 2, p. e124 (2013).

Gooding, M., et al., "Oligonucleotide Conjugates—Candidates for Gene Silencing Therapeutics," European Journal of Pharmaceutics and Biopharmaceutics 107:321-340, Elsevier Science, Netherlands (Oct. 2016).

\* cited by examiner

| Penetratin-Bpep | RQIKIWFQNR | RMKWKKRXRR | BRRXRRBR |
| pVEC-Bpep | LLIILRRRIR | RRBRRXRRBR | |
| Melittin-Bpep | GIGAVLKVLT | KQAHAHSKRX | RRBRRXRRBR |
| Bpep-Bpep | RXRRBRRXRR | KRKRQQRXRR | BRRXRRBR |
| | | BRRXRRBRRX | RRBR |

```
                        SEQUENCE LISTING

<160> NUMBER OF SEQ ID NOS: 18

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aminohexanoic acid
<220> FEATURE:
<221> NAME/KEY: MOD_RES
<222> LOCATION: (21)..(21)
<223> OTHER INFORMATION: bAla
<220> FEATURE:
<221> NAME/KEY: MOD_RES
<222> LOCATION: (24)..(24)
<223> OTHER INFORMATION: Aminohexanoic acid
<220> FEATURE:
<221> NAME/KEY: MOD_RES
<222> LOCATION: (27)..(27)
<223> OTHER INFORMATION: bAla

<400> SEQUENCE: 1

Arg Gln Ile Lys Ile Trp Phe Gln Asn Arg Arg Met Lys Trp Lys Lys
1               5                   10                  15

Arg Xaa Arg Arg Xaa Arg Arg Xaa Arg Arg Xaa Arg
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Aminohexanoic acid
<220> FEATURE:
<221> NAME/KEY: MOD_RES
<222> LOCATION: (23)..(23)
<223> OTHER INFORMATION: bAla
<220> FEATURE:
<221> NAME/KEY: MOD_RES
<222> LOCATION: (26)..(26)
<223> OTHER INFORMATION: Aminohexanoic acid
<220> FEATURE:
<221> NAME/KEY: MOD_RES
<222> LOCATION: (29)..(29)
<223> OTHER INFORMATION: bAla

<400> SEQUENCE: 2

Leu Leu Ile Ile Leu Arg Arg Arg Ile Arg Lys Gln Ala His Ala His
1               5                   10                  15

Ser Lys Arg Xaa Arg Arg Xaa Arg Arg Xaa Arg Arg Xaa Arg
            20                  25                  30
```

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Aminohexanoic acid
<220> FEATURE:
<221> NAME/KEY: MOD_RES
<222> LOCATION: (31)..(31)
<223> OTHER INFORMATION: bAla
<220> FEATURE:
<221> NAME/KEY: MOD_RES
<222> LOCATION: (34)..(34)
<223> OTHER INFORMATION: Aminohexanoic acid
<220> FEATURE:
<221> NAME/KEY: MOD_RES
<222> LOCATION: (37)..(37)
<223> OTHER INFORMATION: bAla

<400> SEQUENCE: 3

Gly Ile Gly Ala Val Leu Lys Val Leu Thr Thr Gly Leu Pro Ala Leu
1               5                   10                  15

Ile Ser Trp Ile Lys Arg Lys Arg Gln Gln Arg Xaa Arg Arg Xaa Arg
            20                  25                  30

Arg Xaa Arg Arg Xaa Arg
        35

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: bAla
<220> FEATURE:
<221> NAME/KEY: MOD_RES
<222> LOCATION: (14)..(14)
<223> OTHER INFORMATION: Aminohexanoic acid
<220> FEATURE:
<221> NAME/KEY: MOD_RES
<222> LOCATION: (17)..(17)
<223> OTHER INFORMATION: bAla
<220> FEATURE:
<221> NAME/KEY: MOD_RES
<222> LOCATION: (20)..(20)
<223> OTHER INFORMATION: Aminohexanoic acid
<220> FEATURE:
<221> NAME/KEY: MOD_RES
<222> LOCATION: (23)..(23)
<223> OTHER INFORMATION: bAla

<400> SEQUENCE: 4

Arg Xaa Arg Arg Xaa Arg Arg Xaa Arg Arg Xaa Arg Arg
1               5                   10                  15

Xaa Arg Arg Xaa Arg Arg Xaa Arg
            20

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg Arg Arg Arg Arg Arg Arg Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: bAla

<400> SEQUENCE: 6

Arg Xaa Arg Arg Xaa Arg Arg Xaa Arg Arg Xaa Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: Aminohexanoic acid
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (11)..(11)
<223> OTHER INFORMATION: Aminohexanoic acid

<400> SEQUENCE: 7

Arg Xaa Arg Arg Xaa Arg Arg Xaa Arg Arg Xaa Arg
1               5                   10

```
<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: bAla

<400> SEQUENCE: 8

Arg Xaa Arg Arg Xaa Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: Aminohexanoic acid

<400> SEQUENCE: 9

Arg Xaa Arg Arg Xaa Arg
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: bAla

<400> SEQUENCE: 10

Arg Xaa Arg Arg Xaa Arg Arg Xaa Arg Arg Xaa Arg
1               5                   10

<210> SEQ ID NO 11
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Leu Ile Ile Leu Arg Arg Arg Ile Arg Lys Gln Ala His Ala His
1               5                   10                  15

Ser Lys

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctattacct taacccag                                                    18

<210> SEQ ID NO 15
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aminohexanoic acid or bAla
<220> FEATURE:
<221> NAME/KEY: MOD_RES
<222> LOCATION: (5)..(5)
<223> OTHER INFORMATION: Aminohexanoic acid or bAla

<400> SEQUENCE: 15

Arg Xaa Arg Arg Xaa Arg
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aminohexanoic acid or bAla
<220> FEATURE:
<221> NAME/KEY: MOD_RES
<222> LOCATION: (5)..(5)
<223> OTHER INFORMATION: Aminohexanoic acid or bAla
<220> FEATURE:
<221> NAME/KEY: MOD_RES
<222> LOCATION: (8)..(8)
<223> OTHER INFORMATION: Aminohexanoic acid or bAla

<400> SEQUENCE: 16

Arg Xaa Arg Arg Xaa Arg Arg Xaa Arg
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aminohexanoic acid or bAla
<220> FEATURE:
<221> NAME/KEY: MOD_RES
<222> LOCATION: (5)..(5)
<223> OTHER INFORMATION: Aminohexanoic acid or bAla
<220> FEATURE:
<221> NAME/KEY: MOD_RES
<222> LOCATION: (8)..(8)
<223> OTHER INFORMATION: Aminohexanoic acid or bAla
<220> FEATURE:
<221> NAME/KEY: MOD_RES
<222> LOCATION: (11)..(11)
<223> OTHER INFORMATION: Aminohexanoic acid or bAla

<400> SEQUENCE: 17

Arg Xaa Arg Arg Xaa Arg Arg Xaa Arg Arg Xaa Arg
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aminohexanoic acid or bAla
<220> FEATURE:
<221> NAME/KEY: MOD_RES
<222> LOCATION: (5)..(5)
<223> OTHER INFORMATION: Aminohexanoic acid or bAla
<220> FEATURE:
<221> NAME/KEY: MOD_RES
<222> LOCATION: (8)..(8)
<223> OTHER INFORMATION: Aminohexanoic acid or bAla
<220> FEATURE:
<221> NAME/KEY: MOD_RES
<222> LOCATION: (11)..(11)
<223> OTHER INFORMATION: Aminohexanoic acid or bAla
```

```
<220> FEATURE:
<221> NAME/KEY: MOD_RES
<222> LOCATION: (14)..(14)
<223> OTHER INFORMATION: Aminohexanoic acid or bAla

<400> SEQUENCE: 18

Arg Xaa Arg Arg Xaa Arg Arg Xaa Arg Arg Xaa Arg Arg Xaa Arg
1               5                   10                  15
```

CHIMERIC PEPTIDES FOR ANTISENSE DELIVERY

CROSS-REFERENCE TO RELATED APPLICATIONS

This application is a 35 U.S.C. § 371 filing of International Application No. PCT/US2019/022475, filed Mar. 15, 2019, which claims priority to U.S. Provisional Application Ser. No. 62/644,202, filed Mar. 16, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 19, 2024, is named 707879-SPT-011US-REPLACEMENT-04192024-ST25.txt and is 8,699 bytes in size.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing, or translation through any one of a number of antisense mechanisms. The sequence specificity of antisense compounds makes them attractive as tools for target validation and gene functionalization, as well as therapeutics to selectively modulate the expression of genes involved in disease.

Although significant progress has been made in the field of antisense technology, there remains a need in the art for oligonucleotides and peptide-oligonucleotide-conjugates having improved antisense or antigene performance.

SUMMARY

Provided herein are chimeric peptide-oligonucleotide-conjugates comprising an oligonucleotide covalently bound to a chimeric peptide (CP). Also provided herein are methods of treating a disease in a subject in need thereof, comprising administering to the subject a chimeric peptide-oligonucleotide-conjugate described herein.

Accordingly, in one aspect, provided herein is a chimeric peptide-oligonucleotide conjugate of Formula I:

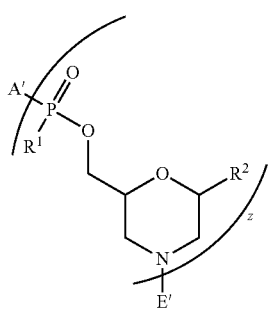

(I)

or a pharmaceutically acceptable salt thereof, wherein:

A' is selected from —NHCH$_2$C(O)NH$_2$, —N(C$_{1-6}$-alkyl)CH$_2$C(O)NH$_2$,

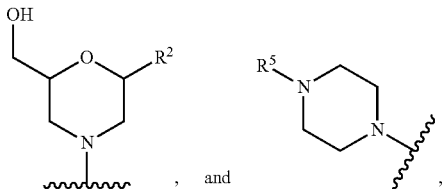

wherein

R$^5$ is —C(O)(O-alkyl)$_x$-OH, wherein x is 3-10 and each alkyl group is, independently at each occurrence, C$_{2-6}$-alkyl, or R$^5$ is selected from —C(O)C$_{1-6}$-alkyl, trityl, monomethoxytrityl, —(C$_{1-6}$-alkyl)-R$^6$, —(C$_{1-6}$-heteroalkyl)-R$^6$, aryl-R$^6$, heteroaryl-R$^6$, —C(O)O—(C$_{1-6}$-alkyl)-R$^6$, —C(O)O-aryl-R$^6$, —C(O)O— heteroaryl-R$^6$, and

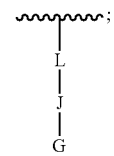

wherein R$^6$ is selected from OH, SH, and NH$_2$, or R$^6$ is O, S, or NH, each of which are covalently-linked to a solid support;

each R$^1$ is independently selected from OH and —N(R$^3$)(R$^4$), wherein each R$^3$ and R$^4$ are, independently at each occurrence, —C$_{1-6}$-alkyl;

each R$^2$ is independently selected from H, a nucleobase, and a nucleobase functionalized with a chemical protecting-group, wherein the nucleobase, independently at each occurrence, comprises a C$_{3-6}$-heterocyclic ring selected from pyridine, pyrimidine, triazinane, purine, and deaza-purine;

z is 8-40; and

E' is selected from H, —C$_{1-6}$-alkyl, —C(O)C$_{1-6}$-alkyl, benzoyl, stearoyl, trityl, monomethoxytrityl, dimethoxytrityl, trimethoxytrityl,

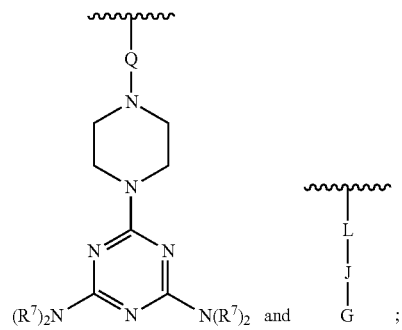

wherein

Q is —C(O)(CH$_2$)$_6$C(O)— or —C(O)(CH$_2$)$_2$S$_2$(CH$_2$)$_2$C(O)—;

R$^7$ is —(CH$_2$)$_2$OC(O)N(R$^8$)$_2$, wherein R$^8$ is —(CH$_2$)$_6$NHC(=NH)NH$_2$;

L is —C(O)(CH$_2$)$_{1-6}$—C$_{1-6}$-heteroaromatic-(CH$_2$)$_{1-6}$C(O), wherein L is covalently-linked by an amide bond to the amino-terminus of J;

J is 2, 3, 4, or 5 covalently-linked cell-penetrating peptides;

G is selected from H, —C(O)C$_{1-6}$-alkyl, benzoyl, and stearoyl, wherein G is covalently-linked by an amide bond to the carboxy-terminus of J; and wherein at least one of the following conditions is true:

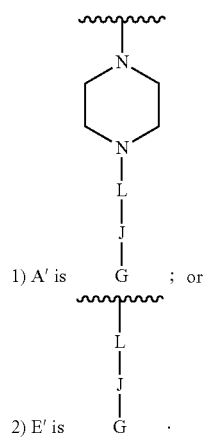

1) A' is G ; or

2) E' is G.

In one embodiment, L is —C(O)(CH$_2$)$_{1-6}$-triazole-(CH$_2$)$_{1-6}$C(O).

In some embodiments, at least one of the cell-penetrating peptides is an amphipathic peptide and at least one of the cell-penetrating peptides is an oligoarginine peptide.

In certain embodiments, one of the cell-penetrating peptides is an amphipathic peptide and one of the cell-penetrating peptides is an oligoarginine peptide.

In one embodiment, J is two covalently-linked cell-penetrating peptides, and wherein one of the cell-penetrating peptides is an amphipathic peptide and one of the cell-penetrating peptides is an oligoarginine peptide.

In one embodiment, the chimeric peptide-oligonucleotide-conjugate of Formula I is a chimeric peptide-oligonucleotide-conjugate of Formula Ia:

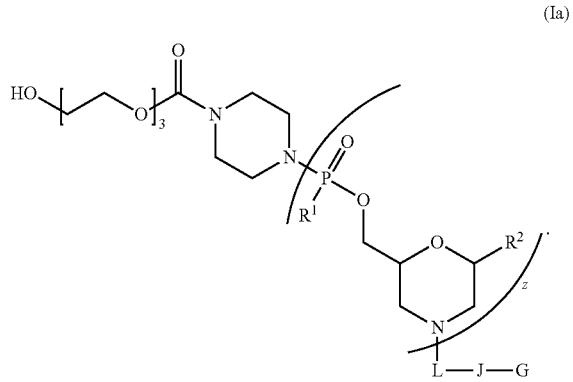

(Ia)

or a pharmaceutically acceptable salt thereof,
wherein J is as defined above.

In some embodiments, at least one of the cell-penetrating peptides is an amphipathic peptide and at least one of the cell-penetrating peptides is an oligoarginine peptide.

In certain embodiments, one of the cell-penetrating peptides is an amphipathic peptide and one of the cell-penetrating peptides is an oligoarginine peptide.

In certain embodiments, J is two covalently-linked cell-penetrating peptides as defined above.

In another embodiment, the chimeric peptide-oligonucleotide-conjugate of Formula I is a chimeric peptide-oligonucleotide-conjugate of Formula Ib:

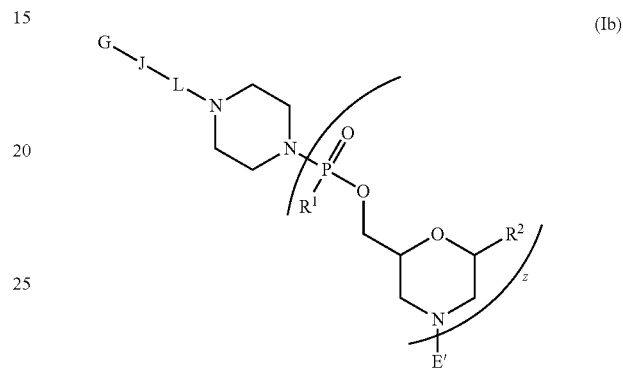

(Ib)

or a pharmaceutically acceptable salt thereof,
wherein J is as defined above.

In some embodiments, at least one of the cell-penetrating peptides is an amphipathic peptide and at least one of the cell-penetrating peptides is an oligoarginine peptide.

In certain embodiments, one of the cell-penetrating peptides is an amphipathic peptide and one of the cell-penetrating peptides is an oligoarginine peptide.

In certain embodiments, two covalently-linked cell-penetrating peptides as defined above In still another aspect, provided herein is a method of treating a muscle disease, a viral infection, a neuromuscular disease, or a bacterial infection in a subject in need thereof, comprising administering to the subject a chimeric peptide-oligonucleotide-conjugate of the present disclosure.

BRIEF DESCRIPTION OF THE FIGURES

FIG. 1 A discloses SEQ ID NOS 1-4, respectively, in order of appearance.

FIG. 1 B) Shows the general structure of a PMO-chimera conjugate. FIG. 1 B discloses SEQ ID NO: 14. FIG. 1 C) Shows a plot demonstrating the mean eGFP fluorescence of a population of stably transfected HeLa 654 cells after continuous treatment for 22 hours with 5 μM of each PMO-peptide conjugate.

FIG. 2 C) Shows the comparison of eGFP mean fluorescence intensity for HeLa 654 cells treated with 5 μM of each base PMO-CPP for 22 hours in the presence or absence of 5 μM Bpep.

FIG. 3 B) Shows a plot of eGFP mean fluorescence intensity for cells treated with different concentrations of chlorpromazine.

FIG. 4 B) Shows live-cell confocal microscopy images of HeLa 654 cells after treatment.

DETAILED DESCRIPTION

Figures 1A, 1B:
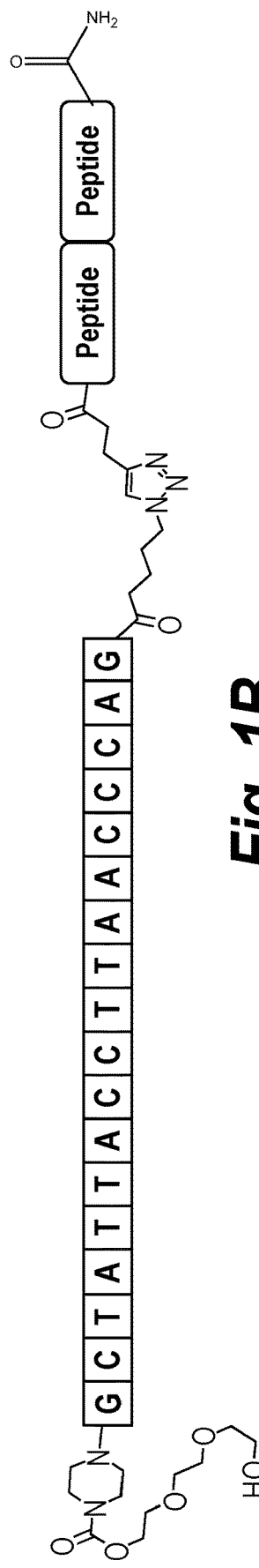
FIG. 1 A) Shows amino acid sequences of four cell-penetrating peptide chimeras described herein.

Phosphorodiamidate morpholino oligonucleotides (PMOs) are attractive therapeutic molecules for genetic diseases. Designed to recognize targets by Watson-Crick base pairing, PMOs exhibit a high level of specificity for their complimentary nucleotide sequence. Depending on the type of sequence targeted, PMOs can mediate a variety of effects, including blocking protein translation or modifying gene splicing. Eteplirsen, a PMO conditionally approved by the FDA to treat Duchenne muscular dystrophy, causes a mutation-containing exon in the pre-mRNA encoding for dystrophin to be excluded from the final protein transcript, restoring protein functionality.

In terms of structure, PMOs are neutral oligonucleotide analogues in which the ribosyl ring has been replaced with a morpholino ring and the negatively-charged phosphodiester backbone has been replaced with the uncharged phosphorodiamidate. The altered backbone structure prevents degradation in both serum and by intracellular nucleases. However, the relatively large size and neutral charge of PMOs can lead to inefficient delivery to the cytosol and nucleus.

Cell-penetrating peptides (CPPs) are a promising strategy to improve the delivery of PMO to the nucleus. CPPs are relatively short sequences of 5-40 amino acids that ideally access the cytosol and can promote the intracellular delivery of cargo. CPPs can be classified into different groups based on their physicochemical properties. One common CPP class consists of repetitive, arginine-based peptides such as $R_{12}$ (SEQ ID NO: 5) and Bpep (RXRRβRRXRRβR (SEQ ID NO: 6), in which X is aminohexanoic acid and β is β-alanine). These oligoarginine peptides are often random coils. When conjugated to PMO, the oligoarginine peptides have been some of the most effective peptides in promoting PMO delivery. Other CPPs, such as Penetratin, pVEC, and melittin, are more amphipathic in nature. While these sequences do contain cationic residues, the defined separation of charged and hydrophobic residues can promote amphipathic helix formation. However, amphipathic CPPs have not been demonstrated to significantly improve PMO efficacy.

No universal mechanism of cell entry exists for CPPs or CPP-PMO conjugates. The mechanism is often highly dependent on the treatment concentrations and the type of cargo attached. Above a certain threshold concentration (generally low micromolar), energy-independent cytosolic uptake can be observed faster than the time scale of endocytosis and cell surface recycling. The fast uptake rate provides evidence for a direct translocation mechanism similar to what is observed for a small molecule. However, at low, physiologically-relevant concentrations, uptake is primarily endocytic. Even within the category of endocytosis, CPPs and CPP-PMO conjugates can enter cells using one or multiple endocytic mechanisms. These endocytic mechanisms include micropinocytosis, clathrin-mediated endocytosis, caveolae-mediated endocytosis and clathrin/caveloae-independent endocytosis. CPP-PMO conjugates are primarily endocytosed at low concentrations, and the CPPs that are poor for PMO delivery are likely trapped in endosomes or excluded from the nuclear compartment.

Provided herein, are chimeric peptide-PMO conjugates for improving PMO delivery. These chimeric peptide-PMO conjugates are comprised of two or more CPPs covalently linked to one another and conjugated with PMOs. An increase in cellular uptake of the oligonucleotide, especially when compared to unconjugated PMOs and single CPP-PMO conjugates, is described herein.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

The term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. In various embodiments, examples of an aryl group may include phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_{6-12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_{1-9}$-heteroaryl indicates the number of carbon atoms contained in the heteroaryl group without including the number of heteroatoms. For example, a $C_{1-9}$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3—, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including. e.g., 2-benzimidazolyl), benzotriazolyl, thioxanthinyl, carbazolyl, carbolinyl, acridinyl, pyrrolizidinyl, and quinolizidinyl.

The term "protecting group" or "chemical protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, monomethoxytrityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particulary useful amine protecting group for the synthesis of compounds of Formula (I) is the trifluoroacetamide. Carboxylic acid reactive moieties may be blocked with oxidatively-removable protective groups such as 2,4-dimethoxybenzyl, while coexisting amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium (0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "nucleobase," "base pairing moiety," "nucleobase-pairing moiety," or "base" refers to the heterocyclic ring portion of a nucleoside, nucleotide, and/or morpholino subunit. Nucleobases may be naturally occurring, or may be modified or analogs of these naturally occurring nucleobases, e.g., one or more nitrogen atoms of the nucleobase may be independently at each occurrence replaced by carbon. Exemplary analogs include hypoxanthine (the base component of the nucleoside inosine); 2,6-diaminopurine; 5-methyl cytosine; C5-propynyl-modified pyrimidines; 10-(9-(aminoethoxy) phenoxazinyl) (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glenresearch.com); Krueger A T et al., Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

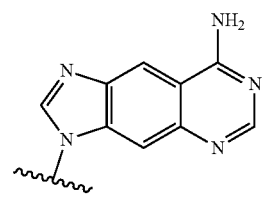

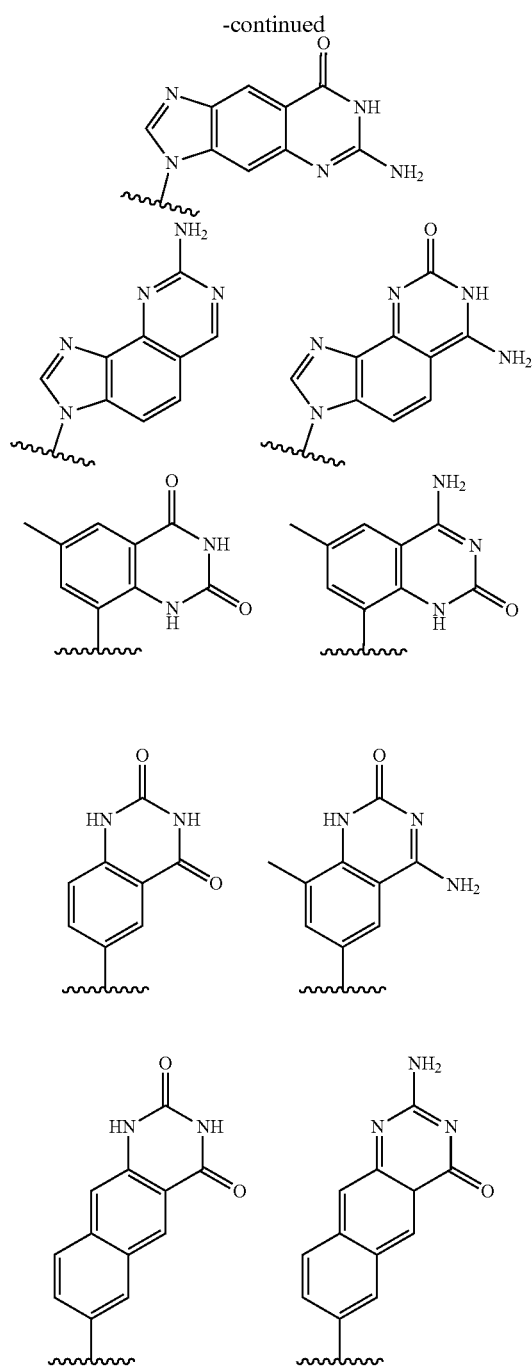

The terms "oligonucleotide" or "oligomer" refer to a compound comprising a plurality of linked nucleosides, nucleotides, or a combination of both nucleosides and nucleotides. In specific embodiments provided herein, an oligonucleotide is a morpholino oligonucleotide.

The phrase "morpholino oligonucleotide" or "PMO" refers to a modified oligonucleotide having morpholino subunits linked together by phosphoramidate or phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The terms "antisense oligomer," "antisense compound" and "antisense oligonucleotide" are used interchangeably and refer to a sequence of subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid: oligomer heteroduplex within the target sequence. The oligomer may have exact (perfect) or near (sufficient) sequence complementarity to the target sequence; variations in sequence near the termini of an oligomer are generally preferable to variations in the interior.

Such an antisense oligomer can be designed to block or inhibit translation of mRNA or to inhibit/alter natural or abnormal pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. In various embodiments, a target sequence may be any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The antisense oligonucleotide and the target RNA are complementary to each other when a sufficient number of corresponding positions in each molecule are occupied by nucleotides which can hydrogen bond with each other, such that stable and specific binding occurs between the oligonucleotide and the target. Thus, "specifically hybridizable" and "complementary" are terms which are used to indicate a sufficient degree of complementarity or precise pairing such that stable and specific binding occurs between the oligonucleotide and the target. It is understood in the art that the sequence of an oligonucleotide need not be 100% complementary to that of its target sequence to be specifically hybridizable. An oligonucleotide is specifically hybridizable when binding of the oligonucleotide to the target molecule interferes with the normal function of the target RNA, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases. In some embodiments, the nucleobase is covalently linked at the N9 atom of the purine base, or at the N1 atom of the pyrimidine base, to the morpholine ring of a nucleotide or nucleoside.

Purine bases comprise a pyrimidine ring fused to an imidazole ring, as described by the general formula:

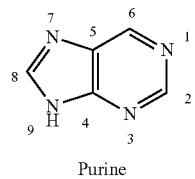

Purine

Adenine and guanine are the two purine nucleobases most commonly found in nucleic acids. These may be substituted with other naturally-occurring purines, including but not limited to N6-methyladenine, N2-methylguanine, hypoxanthine, and 7-methylguanine.

Pyrimidine bases comprise a six-membered pyrimidine ring as described by the general formula:

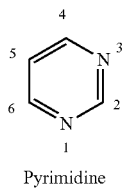

Pyrimidine

Cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), pseudouracil or derivatives thereof; and degenerate or universal bases, like 2,6-difluorotoluene or absent bases like abasic sites (e.g. 1-deoxyribose, 1,2-dideoxyribose, I-deoxy-2-O-methylribose; or pyrrolidine derivatives in which the ring oxygen has been replaced with nitrogen (azaribose)). Pseudouracil is a naturally occurring isomerized version of uracil, with a C-glycoside rather than the regular N-glycoside as in uridine.

Certain modified or substituted nucleobases are particularly useful for increasing the binding affinity of the antisense oligonucleotides of the disclosure. These include 5-substituted pyrimidines, 6-azapyrimidines and N-2, N-6 and 0-6 substituted purines, including 2-aminopropyladenine, 5-propynyluracil and 5-propynylcytosine. In various embodiments, nucleobases may include 5-methylcytosine substitutions, which have been shown to increase nucleic acid duplex stability by 0.6-1.2° C.

In some embodiments, modified or substituted nucleobases are useful for facilitating purification of antisense oligonucleotides. For example, in certain embodiments, antisense oligonucleotides may contain three or more (e.g., 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with hypoxanthine. The substitution of hypoxanthine for one or more guanines in a string of three or more consecutive guanine bases can reduce aggregation of the antisense oligonucleotide, thereby facilitating purification.

The oligonucleotides provided herein are synthesized and do not include antisense compositions of biological origin. The molecules of the disclosure may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution, or absorption, or a combination thereof.

The terms "complementary" and "complementarity" refer to oligonucleotides (i.e., a sequence of nucleotides) related by base-pairing rules. For example, the sequence "T-G-A (5'-3')," is complementary to the sequence "T-C-A (5'-3')." Complementarity may be "partial," in which only some of the nucleic acids' bases are matched according to base pairing rules. Or, there may be "complete," "total," or "perfect" (100%) complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100% complementarity. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5'-terminus, 3'-terminus, or both termini.

The term "peptide" refers to a compound comprising a plurality of linked amino acids. The peptides provided herein can be considered to be cell penetrating peptides.

The terms "cell penetrating peptide" and "CPP" are used interchangeably and refer to cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. In various embodiments, a CPP embodiment of the disclosure may include an arginine-rich peptide as described further below.

As used herein, the term "chimeric peptide" refers to a polypeptide that comprises a first portion that is a first peptide or a fragment thereof, fused to a second portion that is a different peptide or fragment thereof, fused to a third portion and so on. The chimeric peptide can comprise 2, 3, 4, 5, or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond.

As used herein, the term "amphipathic peptide" refers to a peptide with separated regions of essentially charged amino acids and essentially uncharged amino acids. These regions are known as the hydrophilic peptidyl segment and the hydrophobic peptidyl segment, respectively.

As used herein, the term "oligoarginine peptide" refers to a peptide where the peptide is comprised of all arginine or mostly arginine amino acid residues. In certain embodiments, the peptide is comprised entirely of arginine amino acid residues. In certain embodiments, the peptide is comprised of 50-99% arginine amino acid residues interspaced with amino acid linkers, such as, but not limited to, aminohexanoic acid or beta-alanine. In certain embodiments, the peptide is comprised of 75% arginine amino acid residues interspaced with amino acid linkers, such as, but not limited to, aminohexanoic acid or beta-alanine.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

As used herein, "pharmaceutically acceptable salts" refers to derivatives of the disclosed oligonucleotides wherein the parent oligonucleotide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Chimeric Peptide-Oligonucleotide-Conjugates

Provided herein are oligonucleotides chemically linked to a chimeric cell-penetrating peptide. The chimeric cell-penetrating peptide enhances activity, cellular distribution, or cellular uptake of the oligonucleotide. In particular, the chimeric cell-penetrating peptide comprises an amphipathic peptide and an oligoarginine peptide. The oligonucleotides can additionally be chemically-linked to one or more heteroalkyl moieties (e.g., polyethylene glycol) that further enhance the activity, cellular distribution, or cellular uptake of the oligonucleotide. In one exemplary embodiment, the chimeric cell-penetrating peptide is covalently coupled at its N-terminal or C-terminal residue to either end, or both ends, of the oligonucleotide.

Thus, in one aspect, provided herein is a chimeric peptide-oligonucleotide-conjugate of Formula I:

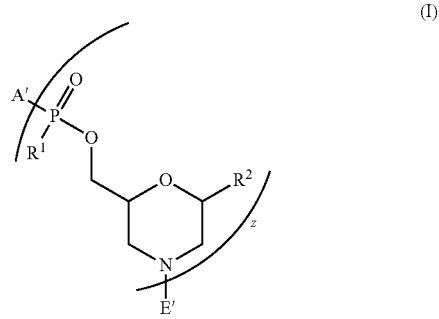

or a pharmaceutically acceptable salt thereof,
wherein:
A' is selected from —NHCH$_2$C(O) NH$_2$, —N(C$_{1-6}$-alkyl) CH$_2$C(O) NH$_2$,

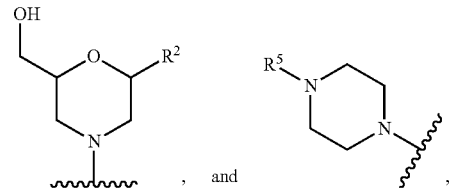

wherein
R$^5$ is —C(O)(O-alkyl), —OH, wherein x is 3-10 and each alkyl group is, independently at each occurrence, C$_{2-6}$-alkyl,
or R$^5$ is selected from —C(O)C$_{1-6}$-alkyl, trityl, monomethoxytrityl, —(C$_{1-6}$-alkyl)-R$^6$, —(C$_{1-6}$-heteroalkyl)-R$^6$, aryl-R$^6$, heteroaryl-R$^6$, —C(O)O—(C$_{1-6}$-alkyl)-R$^6$, —C(O)O-aryl-R$^6$, —C(O)O-heteroaryl-R$^6$, and

wherein R$^6$ is selected from OH, SH, and NH$_2$, or R$^6$ is O, S, or NH, each of which are covalently-linked to a solid support;
each R$^1$ is independently selected from OH and —N(R$^3$)(R$^4$), wherein each R$^3$ and R$^4$ are, independently at each occurrence, —C$_{1-6}$-alkyl;
each R$_2$ is independently selected from H, a nucleobase, and a nucleobase functionalized with a chemical protecting-group, wherein the nucleobase, independently at each occurrence, comprises a $C_{3-6}$-heterocyclic ring selected from pyridine, pyrimidine, triazinane, purine, and deaza-purine;

z is 8-40; and

E' is selected from H, —$C_{1-6}$-alkyl, —$C(O)C_{1-6}$-alkyl, benzoyl, stearoyl, trityl, monomethoxytrityl, dimethoxytrityl, trimethoxytrityl,

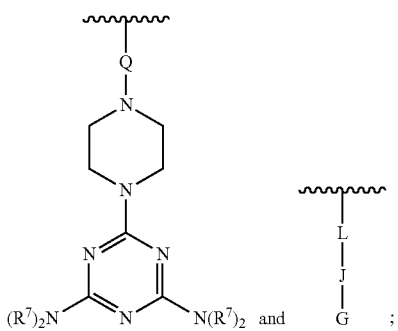

wherein

Q is —$C(O)(CH_2)_6C(O)$— or —$C(O)(CH_2)_2S_2(CH_2)_2C(O)$—;

$R^7$ is —$(CH_2)_2OC(O)N(R^8)_2$, wherein $R^8$ is —$(CH_2)_6NHC(=NH)NH_2$;

L is —$C(O)(CH_2)_{1-6}$—$C_{1-6}$-heteroaromatic-$(CH_2)_{1-6}C(O)$, wherein L is covalently-linked by an amide bond to the amino-terminus of J;

J is 2, 3, 4, or 5 covalently-linked cell-penetrating peptides;

G is selected from H, —$C(O)C_{1-6}$-alkyl, benzoyl, and stearoyl, wherein G is covalently-linked by an amide bond to the carboxy-terminus of J; and wherein at least one of the following conditions is true:

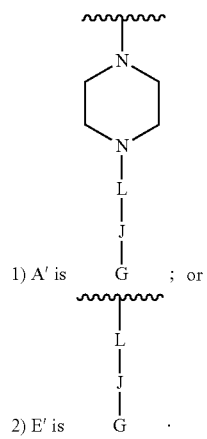

1) A' is G ; or

2) E' is G .

In one embodiment, J is 2, 3, 4, or 5 covalently-linked cell-penetrating peptides, and the cell-penetrating peptides are independently an amphipathic peptide or an oligoarginine peptide.

In some embodiments, at least one of the cell-penetrating peptides is an amphipathic peptide and at least one of the cell-penetrating peptides is an oligoarginine peptide.

In certain embodiments, one of the cell-penetrating peptides is an amphipathic peptide and one of the cell-penetrating peptides is an oligoarginine peptide.

In yet another embodiment, J is two covalently-linked cell-penetrating peptides.

In another embodiment, J is two covalently-linked cell-penetrating peptides, wherein the two cell-penetrating peptides are independently an amphipathic peptide or an oligoarginine peptide.

In still another embodiment, J is two covalently-linked cell-penetrating peptides, wherein one of the cell-penetrating peptides is an amphipathic peptide and one of the cell-penetrating peptides is an oligoarginine peptide.

In yet another embodiment, J is two covalently-linked cell-penetrating peptides, wherein the two cell-penetrating peptides comprise one amphipathic peptide and one oligoarginine peptide, and wherein the oligoarginine peptide is the C-terminus of J and the amphipathic peptide is the N-terminus of J.

In another embodiment, J is two covalently-linked cell-penetrating peptides that are covalently-linked by an amide bond.

In an embodiment, the oligarginine peptide comprises the sequence $[(RY_zR)_x]$ (SEQ ID NOs: 15-18), wherein R is arginine, Y is independently selected from aminohexanoic acid (X) or B-alanine (B), z is 1, and x is 1, 2, 3, 4, or 5.

In still another embodiment, the oligarginine peptide comprises the sequence $[(RXR)(RBR)]_x$ (SEQ ID NOs: 8 and 10) or $[(RBR)(RXR)]_x$; (SEQ ID NOs: 7 and 9), wherein R is arginine, X is aminohexanoic acid, B is B-alanine, and x is 1 or 2.

In another embodiment, the oligoarginine peptide is $[(RXR)(RBR)]_2$ (SEQ ID NO: 10) (Bpep).

In an embodiment, the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

In another embodiment, the hydrophobic segment comprises a sequence of 2 to 10 amino acids independently selected from glycine, isoleucine, alanine, valine, leucine, phenylalanine or tryptophan.

In an embodiment, the hydrophophilic segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

In another embodiment, wherein the amphipathic peptide is pVEC, penetratin, or mellitin melittin.

In another embodiment, the amphipathic peptide is penetratin.

In another embodiment J is penetratin-Bpep (RQIKIWFQNR RMKWKKRXRR BRRXRRBR) (SEQ ID NO: 1), pVEC-Bpep (LLIILRRRIR KQAHAHSKRX RRBRRXRRBR) (SEQ ID NO: 2), melittin-Bpep (GIGAVLKVLT TGLPALISWI KRKRQQRXRR BRRXRRBR) (SEQ ID NO: 3), or Bpep-Bpep (RXRR-BRRXRR BRRXRRBRRX RRBR) (SEQ ID NO: 4), wherein X is aminohexanoic acid and B is beta-alanine.

In still another embodiment, J is penetratin-Bpep (RQIKIWFQNR RMKWKKRXRR BRRXRRBR) (SEQ ID NO: 1), pVEC-Bpep (LLIILRRRIR KQAHAHSKRX RRBRRXRRBR) (SEQ ID NO: 2), or melittin-Bpep (GIGAVLKVLT TGLPALISWI KRKRQQRXRR BRRXRRBR) (SEQ ID NO: 3), wherein X is aminohexanoic acid and B is beta-alanine.

In yet another embodiment, J is penetratin-Bpep (RQIKIWFQNR RMKWKKRXRR BRRXRRBR) (SEQ ID NO: 1), wherein X is aminohexanoic acid and B is beta-alanine.

In a further embodiment, J is pVEC-Bpep (LLIILRRRIR KQAHAHSKRX RRBRRXRRBR) (SEQ ID NO: 2), wherein X is aminohexanoic acid and B is beta-alanine.

In an embodiment, E' is selected from H, —C$_{1-6}$-alkyl, —C(O)C$_{1-6}$-alkyl, benzoyl, stearoyl, trityl, monomethoxytrityl, dimethoxytrityl, trimethoxytrityl, and

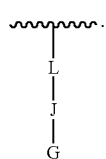

In another embodiment, A' is selected from —N(C$_{1-6}$-alkyl)CH$_2$C(O)NH$_2$.

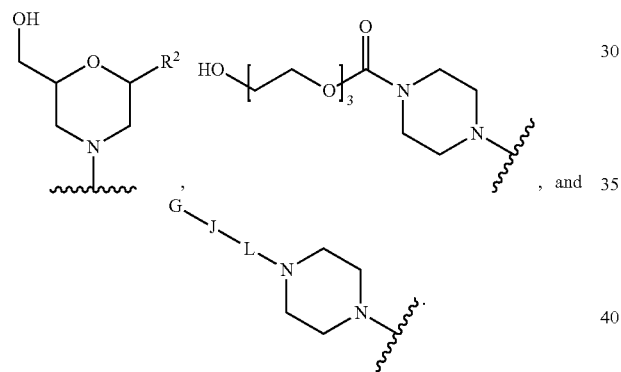

In a further embodiment, E' is selected from H, —C(O)CH$_3$, benzoyl, stearoyl, trityl, 4-methoxytrityl, and

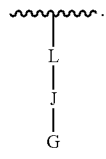

In an embodiment, A' is selected from —N(C$_1$-alkyl)CH$_2$C(O) NH$_2$,

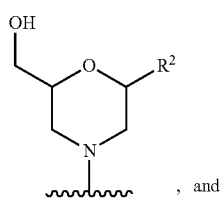, and

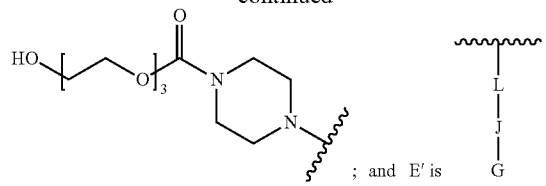; and E' is

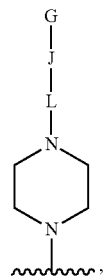.

In another embodiment, A' is

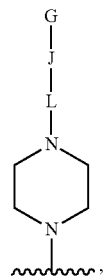, and

E' is selected from H, —C(O)CH$_3$, trityl, 4-methoxytrityl, benzoyl, and stearoyl.

In an embodiment, the chimeric peptide-oligonucleotide conjugate of Formula I is a chimeric peptide-oligonucleotide conjugate of Formula Ia:

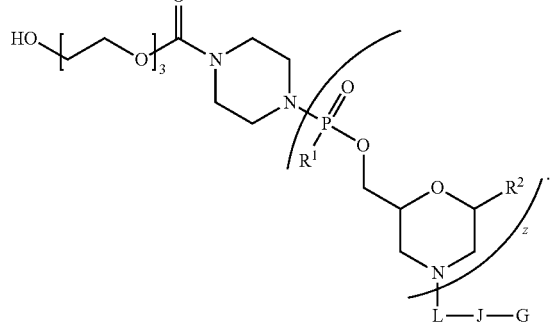

(Ia)

In an embodiment, the chimeric peptide-oligonucleotide conjugate of Formula I is a chimeric peptide-oligonucleotide conjugate of Formula Ib:

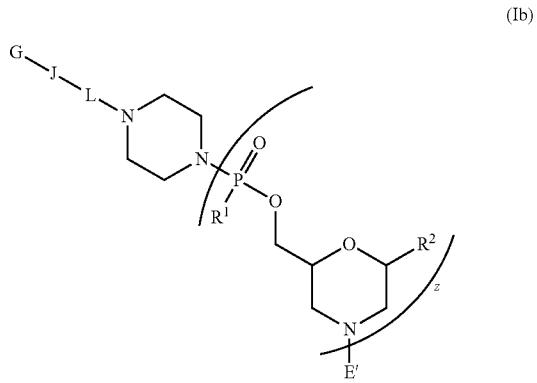

(Ib)

wherein E' is selected from H, $C_{1-6}$-alkyl, —C(O)CH$_3$, benzoyl, and stearoyl.

In still another embodiment of Formula I, Ia, and Ib, each $R^1$ is $N(CH_3)_2$.

In yet another embodiment of Formula I, Ia, and Ib, each $R_2$ is a nucleobase, wherein the nucleobase independently at each occurrence comprises a $C_{4-6}$-heterocyclic ring selected from pyridine, pyrimidine, triazinane, purine, and deaza-purine.

In another embodiment of Formula I, Ia, and Ib, each $R_2$ is a nucleobase, wherein the nucleobase independently at each occurrence comprises a $C_{4-6}$-heterocyclic ring selected from pyrimidine, purine, and deaza-purine.

In still another embodiment of Formula I, Ia, and Ib, each $R_2$ is a nucleobase independently at each occurrence selected from adenine. 2,6-diaminopurine, 7-deaza-adenine, guanine, 7-deaza-guanine, hypoxanthine, cytosine, 5-methyl-cytosine, thymine, uracil, and hypoxanthine.

In yet another embodiment of Formula I, Ia, and Ib, each $R_2$ is a nucleobase independently at each occurrence selected from adenine, guanine, cytosine, 5-methyl-cytosine, thymine, uracil, and hypoxanthine.

In another embodiment of Formula I, Ia, and Ib, L is —C(O)(CH$_2$)$_{1-6}$-triazole-(CH$_2$)$_{1-6}$C(O)—.

In another embodiment of Formula I, Ia, and Ib, L is

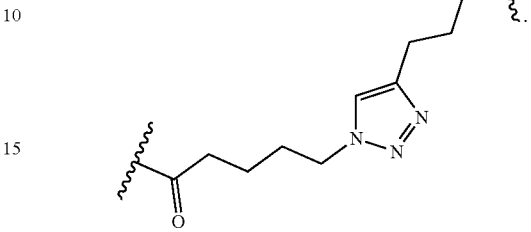

In another embodiment of Formula I, Ia, and Ib, G is selected from H, C(O)CH$_3$, benzoyl, and stearoyl.

In still another embodiment of Formula I, Ia, and Ib, G is H or —C(O)CH$_3$.

In yet another embodiment of Formula I, Ia, and Ib, G is H.

In yet another embodiment of Formula I, Ia, and Ib, G is —C(O)CH$_3$.

In yet another embodiment of Formula I, Ia, and Ib, the chimeric oligonucleotide-peptide conjugate demonstrates at least a 20-fold improvement in uptake as compared to unconjugated oligonucleotide.

In an embodiment, the chimeric oligonucleotide-peptide conjugate demonstrates at least a two-fold improvement in uptake as compared to non-chimeric oligonucleotide-peptide conjugates.

In another embodiment, the chimeric oligonucleotide-peptide conjugate demonstrates improvement in uptake as compared to the corresponding non-chimeric penetratin-peptide conjugate.

Representative peptide-oligonucleotide-conjugates of the disclosure include, amongst others, chimeric peptide-oligonucleotide-conjugates of the following structure:

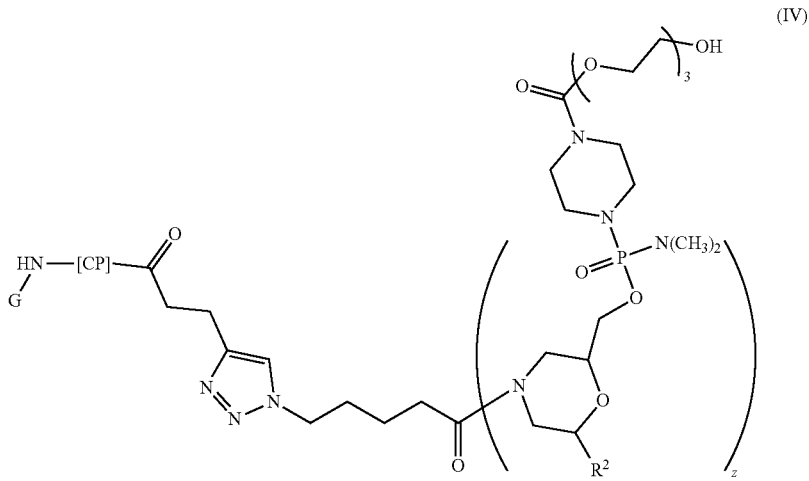

(IV)

or a pharmaceutically acceptable salt thereof, wherein G is H or —C(O)CH$_3$;

R$^2$ is a nucleobase, independently at each occurrence, selected from adenine, guanine, cytosine, 5-methyl-cytosine, thymine, uracil, and hypoxanthine;

z is 8-40; and

CP is, independently at each occurrence, selected from penetratin-Bpep (RQIKIWFQNR RMKWKKRXRR BRRXRRBR) (SEQ ID NO: 1), pVEC-Bpep (LLIILRRRIR KQAHAHSKRX RRBRRXRRBR) (SEQ ID NO: 2), melittin-Bpep (GIGAVLKVLT TGL-PALISWI KRKRQQRXRR BRRXRRBR) (SEQ ID NO: 3), or Bpep-Bpep (RXRRBRRXRR BRRXRR-BRRX RRBR) (SEQ ID NO: 4), wherein X is amino-hexanoic acid and B is beta-alanine.

In an embodiment, G is covalently linked by an amide bond to the carboxy terminus of the peptide.

In one embodiment of the chimeric peptide-oligonucle-otide-conjugates of the disclosure, G is H.

In another embodiment of the chimeric peptide-oligo-nucleotide-conjugates of the disclosure. G is —C(O)CH$_3$.

In an embodiment of Formulae I, Ia, and Ib, L is cova-lently linked by an amide bond to the carboxy terminus of the peptide, and G is covalently linked to the amino terminus of the peptide.

As used herein, "G is covalently linked by an amide bond to the carboxy-terminus of J," indicates that the carboxy-terminus of J (—COOH) is covalently bound to variable G via an N(H) group, wherein the hydroxyl group of the carboxy-terminus of J is replaced with N(H). For example, when G is H, the following structure is formed by J and G:

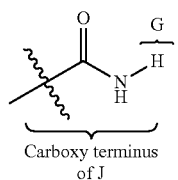

Carboxy terminus of J

In some embodiments, the chimeric peptide-oligonucle-otide-conjugates described herein are unsolvated. In other embodiments, one or more of the chimeric peptide-oligo-nucleotide-conjugates are in solvated form. As known in the art, the solvate can be any of pharmaceutically acceptable solvent, such as water, ethanol, and the like.

Although the chimeric peptide-oligonucleotide-conju-gates of Formulae I, Ia, Ib, II, IIa and IV are depicted in their neutral forms, in some embodiments, these peptide-oligo-nucleotide-conjugates are used in a pharmaceutically acceptable salt form.

Oligonucleotides

Important properties of morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA, T$_M$ values above about 45° C. in relatively short oligonucleotides (e.g., 10-15 bases); 3) the ability of the oligonucleotide to be actively or passively transported into mammalian cells; and 4) the ability of the oligonucleotide and oligonucleotide: RNA heteroduplex to resist RNAse and RNase H degradation, respectively.

The stability of the duplex formed between an oligomer and a target sequence is a function of the binding T$_M$ and the susceptibility of the duplex to cellular enzymatic cleavage. The T$_M$ of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybrid-ization Techniques, Methods Enzymol. Vol. 154 pp. 94-107. In certain embodiments, antisense oligomers may have a binding T$_M$, with respect to a complementary-sequence RNA, of greater than body temperature and, in some embodiments greater than about 45° C. or 50° C. TMS in the range 60-80° C. or greater are also included. According to well-known principles, the T$_M$ of an oligomer, with respect to a complementary-based RNA hybrid, can be increased by increasing the ratio of C:G paired bases in the duplex, or by increasing the length (in base pairs) of the heteroduplex, or both. At the same time, for purposes of optimizing cellular uptake, it may be advantageous to limit the size of the oligomer. For this reason, compounds of the disclosure include compounds that show a high T$_M$ (45-50° C. or greater) at a length of 25 bases or less.

The length of an oligonucleotide may vary so long as it is capable of binding selectively to the intended location within the pre-mRNA molecule. The length of such sequences can be determined in accordance with selection procedures described herein. Generally, the oligonucleotide will be from about 8 nucleotides in length up to about 50 nucleotides in length. For example, the length of the oligo-nucleotide (z) can be 8-38, 8-25, 15-25, 17-21, 20-25, 20-30, 18-23, 19-24, 21-26, 22-27, 23-28, 24-29, 25-30, 26-31, or about 18. In some embodiments, the length can be 10, 11, 17, 18, 19, 20, 21, 22, 23, 24, 25, 26, 27, 28, 29, 30, or 31 nucleotides. It will be appreciated however that any length of nucleotides within these ranges may be used in the methods described herein.

In some embodiments, the antisense oligonucleotides contain base modifications or substitutions. For example, certain nucleo-bases may be selected to increase the binding affinity of the antisense oligonucleotides described herein. These include 5-substituted pyrimidines, 6-azapyrimidines and N-2, N-6 and 0-6 substituted purines, including 2-ami-nopropyladenine, 5-propynyluracil, 5-propynylcytosine and 2,6-diaminopurine. 5-methylcytosine substitutions have been shown to increase nucleic acid duplex stability by 0.6-1.2° C., and may be incorporated into the antisense oligonucleotides described herein. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodi-ment, at least one purine base of the oligonucleotide com-prises an N-2, N-6 substituted purine base. In one embodi-ment, the N-2, N-6 substituted purine base is 2,6-diaminopurine.

Morpholino-based oligomers (including antisense oli-gomers) and synthesis thereof are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; PCT Publication Nos. WO/2009/064471, WO/2012/043730, WO 2017/205513, WO 2017205879, WO 2017/205880, and Summerton et al. 1997, Antisense and Nucleic Acid Drug Development, 7, 187-195, which are hereby incorporated by reference in their entirety.

Accordingly, in one aspect, provided herein is an oligonucleotide of Formula II:

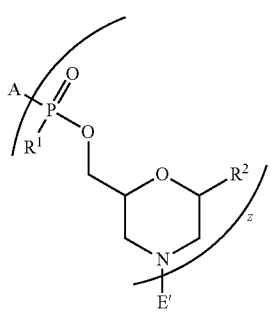

(II)

or a pharmaceutically acceptable salt thereof, wherein

A is selected from the group consisting of OH, —NHCH$_2$C(O) NH$_2$, —N(C$_{1-6}$-alkyl) CH$_2$C(O) NH$_2$,

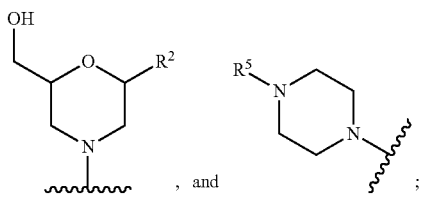

, and ;

R$^5$ is —C(O)(O-alkyl)$_x$OH, wherein x is 3-10 and each alkyl group is independently at each occurrence —C$_{2-6}$-alkyl, or R$^5$ is selected from the group consisting of —C(O)C$_{1-6}$-alkyl, trityl, monomethoxytrityl, —C$_{1-6}$-alkyl-R$^6$, —C$_{1-6}$-heteroalkyl-R$^6$, -aryl-R$^6$, -heteroaryl-R$^6$, —C(O)O—C$_{1-6}$-alkyl-R$^6$, —C(O)O-aryl-R$^6$, and —C(O)O-heteroaryl-R$^6$;

R$^6$ is selected from the group consisting of OH, SH, and NH$_2$, or R$^6$ is O, S, or NH, covalently linked to a solid support;

each R$^1$ is independently OH or —NR$^3$R$^4$;

each R$^3$ and R$^4$ are independently at each occurrence —C$_{1-6}$-alkyl;

each R$_2$ is independently selected from the group consisting of H, a nucleobase, and a nucleobase functionalized with a chemical protecting-group, wherein the nucleobase independently at each occurrence comprises a C$_{3-6}$-heterocyclic ring selected from the group consisting of pyridine, pyrimidine, triazinane, purine, and deaza-purine;

z is 8-40;

E is selected from the group consisting of H, —C$_{1-6}$-alkyl, —C(O)C$_{1-6}$-alkyl, benzoyl, stearoyl, trityl, monomethoxytrityl, dimethoxytrityl, trimethoxytrityl, and

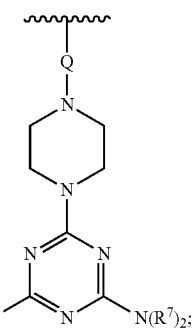

Q is —C(O)(CH$_2$)$_6$C(O)— or —C(O)(CH$_2$)$_2$S$_2$(CH$_2$)$_2$C(O)—;

R$^7$ is —(CH$_2$)$_2$OC(O)N(R$^8$)$_2$;

R$^8$ is —(CH$_2$)$_6$NHC(=NH)NH$_2$.

In one embodiment of Formula II, A is

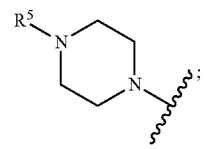

E is selected from the group consisting of H, —C(O)CH$_3$, benzoyl, and stearoyl;

R$^5$ is —C(O)(O-alkyl)$_x$-OH, wherein each alkyl group is independently at each occurrence —C$_{2-6}$-alkyl, trityl, and 4-methoxytrityl; and each R$^2$ is independently a nucleobase, wherein the nucleobase independently at each occurrence comprises a C$_{4-6}$-heterocyclic ring selected from the group consisting of pyridine, pyrimidine, purine, and deaza-purine.

In another embodiment of Formula II, R$^5$ is C(O)(O—CH$_2$CH$_2$) 3-OH; and each R$^2$ is independently a nucleobase, wherein the nucleobase independently at each occurrence comprises a pyrimidine or a purine.

In still another embodiment, the oligonucleotide of Formula II is an oligonucleotide of Formula IIa:

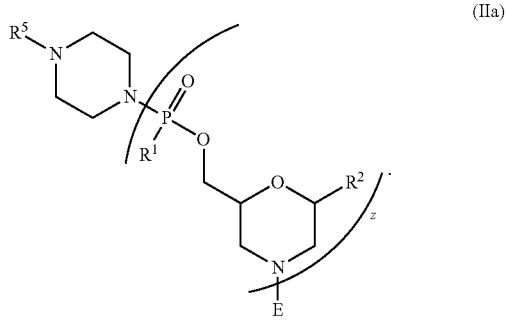

(IIa)

In an embodiment of Formula II and IIa, R$^2$ is independently at each occurrence adenine, 2,6-diaminopurine, guanine, hypoxanthine, cytosine, 5-methyl-cytosine, thymine, uracil, and hypoxanthine; and each R$^1$ is —N(CH$_3$)$_2$.

Provided in Table 1 are various embodiments of nucleotide moieties as described herein.

TABLE 1

Various embodiments of nucleotide moieties.

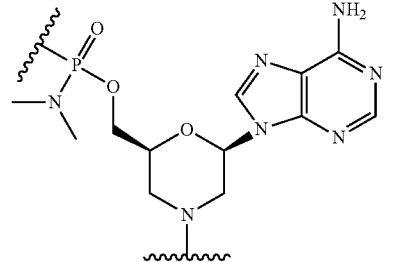 [SMILES: *N1C[C@@H](COP(*)(=O)N(C)C)O[C@@H](n2cnc3c(N)ncnc32)C1]

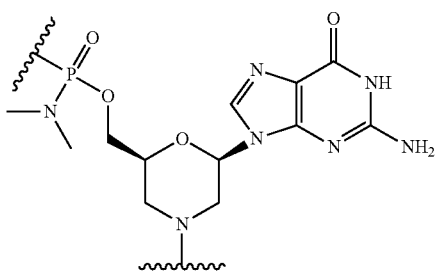 [SMILES: *N1C[C@@H](COP(*)(=O)N(C)C)O[C@@H](n2cnc3c(=O)[nH]c(N)nc32)C1]

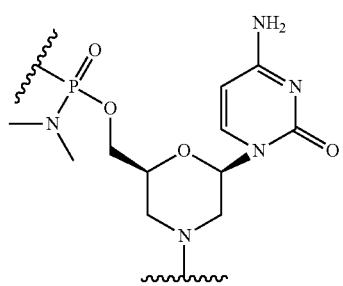 [SMILES: *N1C[C@@H](COP(*)(=O)N(C)C)O[C@@H](n2ccc(N)nc2=O)C1]

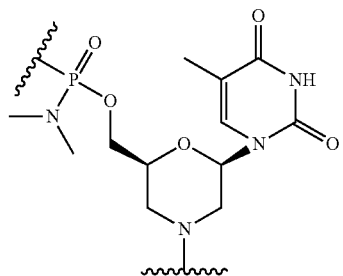 [SMILES: *N1C[C@@H](COP(*)(=O)N(C)C)O[C@@H](n2cc(C)c(=O)[nH]c2=O)C1]

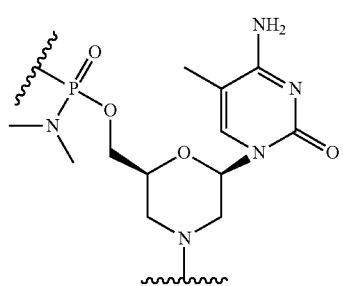 [SMILES: *N1C[C@@H](COP(*)(=O)N(C)C)O[C@@H](n2cc(C)c(N)nc2=O)C1]

TABLE 1-continued

Various embodiments of nucleotide moieties.

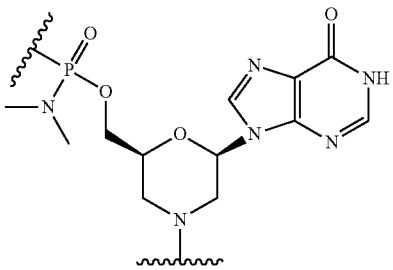 [SMILES: *N1C[C@@H](COP(*)(=O)N(C)C)O[C@@H](n2cnc3c(=O)[nH]cnc32)C1]

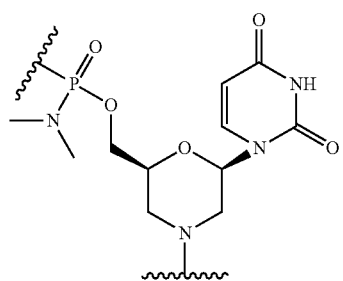 [SMILES: *N1C[C@@H](COP(*)(=O)N(C)C)O[C@@H](n2ccc(=O)[nH]c2=O)C1]

In some embodiments, the oligonucleotides described herein are unsolvated. In other embodiments, one or more of the oligonucleotides are in solvated form. As known in the art, the solvate can be any of pharmaceutically acceptable solvent, such as water, ethanol, and the like.

Although the oligonucleotides of Formulas II and IIa, are depicted in their neutral forms, in some embodiments, these oligonucleotides are used in a pharmaceutically acceptable salt form.

Chimeric Peptides

The oligonucleotides provided herein include an oligonucleotide moiety conjugated to a chimeric peptide. In particular, the chimeric peptide is two covalently-linked cell-penetrating peptides, and wherein the two cell-penetrating peptides are independently an amphipathic peptide or an oligoarginine peptide.

In some embodiments, the two cell-penetrating peptides comprise one amphipathic peptide and one oligoarginine peptide, and wherein the oligoarginine peptide is the C-terminus of chimeric peptide and the amphipathic peptide is the N-terminus of chimeric peptide.

In some embodiments, at least one of the cell-penetrating peptides is an amphipathic peptide and at least one of the cell-penetrating peptides is an oligoarginine peptide.

In certain embodiments, one of the cell-penetrating peptides is an amphipathic peptide and one of the cell-penetrating peptides is an oligoarginine peptide.

A representation of such a chimeric peptide is shown below:

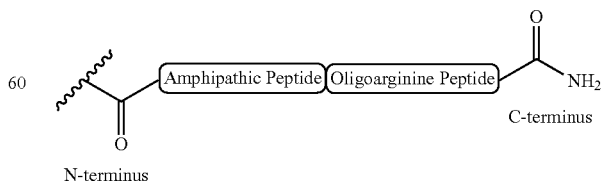

wherein the N-terminus is covalently attached to an oligonucleotide.

In particular embodiments, the two covalently-linked cell-penetrating peptides are covalently-linked by an amide bond.

In some embodiments, the chimeric peptide can be effective to enhance transport of the compound into cells. The transport moiety is, in some embodiments, attached to a terminus of the oligomer. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration.

The transport moieties as described above have been shown to greatly enhance cell entry of attached oligomers, relative to uptake of the oligomer in the absence of the attached transport moiety. Uptake may be enhanced at least three fold, and, in some embodiments, 50 fold, relative to the unconjugated compound. In some embodiments, uptake may be enhanced, and, in some embodiments, three fold, relative to the non-chimeric oligonucleotide-peptide conjugates.

The use of chimeric peptides are particularly useful in practicing the present disclosure. Certain chimeric peptide transporters have been shown to be highly effective at delivery of antisense compounds into primary cells including muscle cells. Furthermore, the chimeric peptide transporters described herein, when conjugated to an antisense PMO, demonstrate an enhanced ability to alter splicing of several gene transcripts.

Thus, in one aspect, provided herein is a chimeric peptide that is 2, 3, 4, or 5 covalently-linked cell-penetrating peptides, or a pharmaceutically acceptable salt thereof.

In an embodiment, each chimeric peptide is 2, 3, 4, or 5 covalently-linked cell-penetrating peptides, wherein the cell-penetrating peptides are independently an amphipathic peptide or an oligoarginine peptide.

In another embodiment, each chimeric peptide is two covalently-linked cell-penetrating peptides.

In another embodiment, each chimeric peptide is two covalently-linked cell-penetrating peptides, wherein the two cell-penetrating peptides are independently an amphipathic peptide or an oligoarginine peptide.

In another embodiment, each chimeric peptide is two covalently-linked cell-penetrating peptides, wherein one of the cell-penetrating peptides is an amphipathic peptide and one of the cell-penetrating peptides is an oligoarginine peptide.

In still another embodiment, each chimeric peptide is two covalently-linked cell-penetrating peptides, wherein the two cell-penetrating peptides comprise one amphipathic peptide and one oligoarginine peptide, and wherein the oligoarginine peptide is the C-terminus of J and the amphipathic peptide is the N-terminus of J In yet another embodiment, each chimeric peptide is two covalently-linked cell-penetrating peptides that are covalently-linked by an amide bond.

In another embodiment, the oligarginine peptide comprises the sequence $[(RY_zR)_x]$ (SEQ ID NOs: 15-18), wherein R is arginine, Y is independently selected from aminohexanoic acid (X) or B-alanine (B), z is 1, and x is 1, 2, 3, 4, or 5.

In yet another embodiment, the oligarginine peptide of the chimeric peptide comprises the sequence $[(RXR)(RBR)]_x$ (SEQ ID NOs: 8 and 10) or $[(RBR)(RXR)]_x$ (SEQ ID NOs: 7 and 9), wherein R is arginine, X is aminohexanoic acid, B is B-alanine, and x is 1 or 2.

In still another embodiment, the oligoarginine peptide of the chimeric peptide is $[(RXR)(RBR)]_2$ (SEQ ID NO: 10) (Bpep).

In another embodiment, the amphipathic peptide of the chimeric peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

In a particular embodiment, the hydrophobic segment comprises a sequence of 2 to 10 amino acids independently selected from glycine, isoleucine, alanine, valine, leucine, phenylalanine or tryptophan.

In a particular embodiment, the hydrophophilic segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

In an embodiment, the amphipathic peptide of the chimeric peptide is pVEC, penetratin, or mellitin.

In an embodiment, the amphipathic peptide of the chimeric peptide is penetratin.

In an embodiment, the chimeric peptide is penetratin-Bpep (RQIKIWFQNR RMKWKKRXRR BRRXRRBR) (SEQ ID NO: 1), pVEC-Bpep (LLIILRRRIR KQAHAHS-KRX RRBRRXRRBR) (SEQ ID NO: 2), melittin-Bpep (GIGAVLKVLT TGLPALISWI KRKRQQRXRR BRRXRRBR) (SEQ ID NO: 3), or Bpep-Bpep (RXRR-BRRXRR BRRXRRBRRX RRBR) (SEQ ID NO: 4).

In an embodiment, the chimeric peptide is penetratin-Bpep (RQIKIWFQNR RMKWKKRXRR BRRXRRBR) (SEQ ID NO: 1), pVEC-Bpep (LLIILRRRIR KQAHAHS-KRX RRBRRXRRBR) (SEQ ID NO: 2), or melittin-Bpep (GIGAVLKVLT TGLPALISWI KRKRQQRXRR BRRXRRBR) (SEQ ID NO: 3).

In an embodiment, the chimeric peptide is penetratin-Bpep (RQIKIWFQNR RMKWKKRXRR BRRXRRBR) (SEQ ID NO: 1).

In some embodiments, the chimeric peptides described herein are unsolvated. In other embodiments, one or more of the chimeric peptides are in solvated form. As known in the art, the solvate can be any of pharmaceutically acceptable solvent, such as water, ethanol, and the like.

Although the chimeric peptides, are depicted in their neutral forms, in some embodiments, these oligonucleotides are used in a pharmaceutically acceptable salt form.

Methods

Provided herein are methods of treating a neuromuscular disease, a muscle disease, a viral infection, or a bacterial infection in a subject in need thereof, comprising administering to the subject a peptide-oligonucleotide-conjugate of Formulae I, Ia, or Ib.

Accordingly, in one aspect, provided herein is a method of treating a muscle disease, a viral infection, a neuromuscular disease or a bacterial infection in a subject in need thereof, comprising administering to the subject a chimeric peptide-oligonucleotide-conjugate of the present disclosure.

In one embodiment, the neuromuscle disease is Duchenne Muscular Dystrophy.

In another embodiment, the viral infection is caused by a virus selected from the group consisting of marburg virus, ebola virus, influenza virus, and dengue virus.

In another embodiment, the bacterial infection is caused by *Mycobacterium tuberculosis*.

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g/kg of body weight, once or more daily, to once every 20 years.

In some embodiments, the oligonucleotide (an oligonucleotide of Formulae II or IIa) is administered alone.

In some embodiments, the oligonucleotide is administered in a therapeutically effective amount or dosage. A "therapeutically effective amount" is an amount of an oligonucleotide of Formula II or IIa that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the oligonucleotide that corresponds to a therapeutically effective amount is strongly dependent on the type of disease, stage of the disease, the age of the patient being treated, and other facts.

In different embodiments, depending on the oligonucleotide of Formulae II or IIa and the effective amounts used, the oligonucleotides can modulate the expression of a gene involved in a muscle disease, a viral infection, or a bacterial infection.

While the amounts of an oligonucleotide of Formulae II or IIa should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

Oligonucleotides of Formula II and IIa, or their pharmaceutically acceptable salts or solvate forms, in pure form or in an appropriate pharmaceutical composition, can be administered via any of the accepted modes of administration or agents known in the art. The oligonucleotides can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active oligonucleotide or oligonucleotides in a certain part of the intestinal tract in a delayed manner. Examples of embedded compositions that can be used are polymeric substances and waxes. The active oligonucleotides also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the conjugates described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the oligonucleotides described herein, or a pharmaceutically acceptable salt thereof, and 99% to 1% by weight of a pharmaceutically acceptable excipient. In one example, the composition will be between about 5% and about 75% by weight of a oligonucleotide described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising oligonucleotides, peptides, peptide-oligonucleotide-conjugates, or compositions of the disclosure. In some embodiments, kits comprise a peptide-oligonucleotide-conjugate according to Formulae I, Ia, or Ib, or a pharmaceutically acceptable salt thereof. In other embodiments, kits comprise an oligonucleotide according to Formulae II or IIa, or a pharmaceutically acceptable salt thereof. In still other embodiments, kits comprise a peptide according to Formula III, or a pharmaceutically acceptable salt thereof.

The phrase "package" means any vessel containing oligonucleotides or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering oligonucleotides or compositions of the disclosure to a patient. Kits also can comprise instructions for approved uses of oligonucleotides herein by regulatory agencies, such as the United States Food and Drug Administration. Kits can also contain labeling or product inserts for the oligonucleotides. The package(s) or any product insert(s), or both, may themselves be approved by regulatory agencies. The kits can include oligonucleotides in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Chimeric peptides composed of a random-coil, oligoarginine CPP with an amphipathic CPP can improve PMO activity. If each CPP utilizes distinct mechanisms of endocytosis, the chimera may be able to access multiple mechanisms of cellular entry. Further the different CPPs may have beneficial effects on processes downstream of uptake, such as endosomal escape or nuclear entry. Herein are several amphipathic/oligoarginine CPP chimeras that exhibited a synergistic, rather than additive, gain in PMO efficacy in a biological assay. The CPP chimeras outperform the potent CPP standard (Bpep) for PMO activity in this assay.

The conjugates were evaluated in the HeLa-654 eGFP assay to assess if the chimeric CPPs would improve PMO efficacy. In this assay, the Hela cells are stably transfected with an eGFP sequence that is interrupted with a mutated intron of the human β-globin gene (IVS2-654). The mutation creates a cryptic splice site that leads to retention of a β-globin fragment in the eGFP mRNA sequence. Upon translation, the eGFP is nonfluorescent. The IVS2-654 PMO utilized in the conjugates hybridizes to the mutated intron and prevents the aberrant gene splicing, leading to an eGFP mRNA sequence that encodes for functional, fluorescent eGFP. The amount of PMO delivered is therefore correlated to the amount of functional eGFP expressed.

The HeLa-654 eGFP cells were treated with 5 µM of each conjugate in serum-containing media. After 22 hours, the fluorescence of the cells was analyzed by flow cytometry (FIG. 1C). All four CPP chimeras performed better than Bpep, the consistently high-performing CPP for PMO delivery. The top performing chimera, PMO-Penetratin-Bpep had an approximately 70-fold increase in eGFP fluorescence compared to the background fluorescence of untreated cells. For reference, this is over a 20-fold improvement with respect to the unconjugated PMO and a two-fold improvement with respect to PMO-Bpep.

Both PMO-Penetratin-Bpep and PMO-pVEC-Bpep displayed synergy, in which the activity of the PMO-chimeric CPP was greater than the sum of the expected activities from each of the PMO-CPPs individually. For example, PMO-Penetratin demonstrated a 7-fold increase and PMO-Bpep demonstrated a 35-fold increase in eGFP fluorescence. An additive effect would lead to a 42-fold increase in eGFP fluorescence for PMO-Penetratin-Bpep. However, the PMO-Penetratin-Bpep chimera had an almost 70-fold increase in eGFP fluorescence, meaning it performed approximately 1.5 times better than an additive effect. A similar synergy was also observed for PMO-pVEC-Bpep, in which the measured eGFP fluorescence was also 1.5 times greater than the sum of the parts.

Figure 2A:
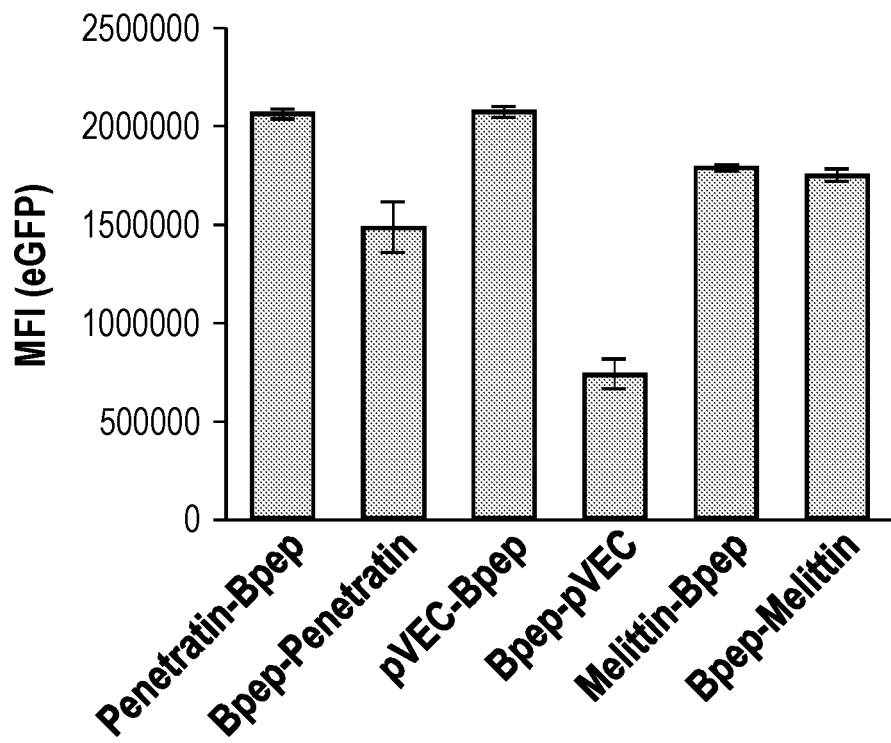
FIG. 2A) Shows the activity of the PMO-peptide conjugate measured in a eGFP assay, as well as the activity of each chimera in reversal.
Figure 2B:
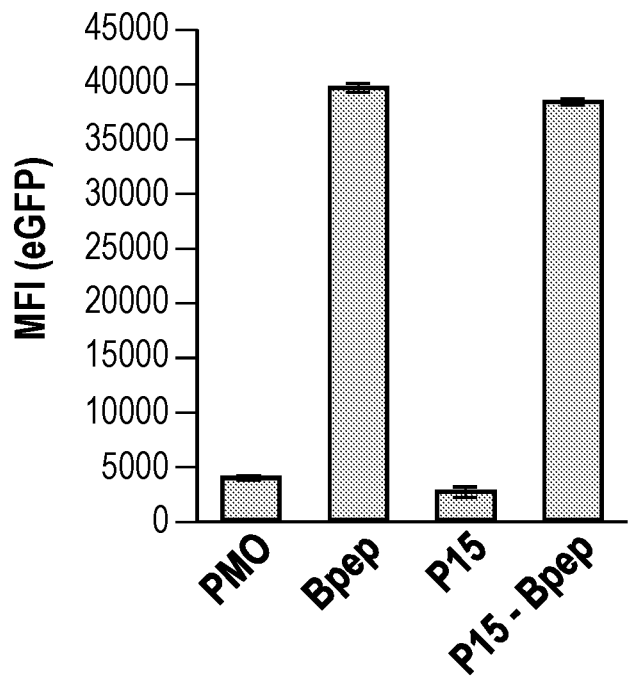
FIG. 2 B) Shows the mean fluorescence intensity of eGFP for cells treated with 5 μM of PMO, PMO-P15, PMO-Bpep or PMO-P15Bpep for 22 hours. P15 is a peptide consisting of 15 proline amino acid residues.

Interestingly, for both synergistic chimeras (PMO-Penetratin-Bpep and PMO-pVEC-Bpep), switching the order of the peptides decreased the mean fluorescence observed (FIG. 2A). This observation suggests that it is critical to have Bpep as the C-terminal component to observe synergy.

Figure 2C:
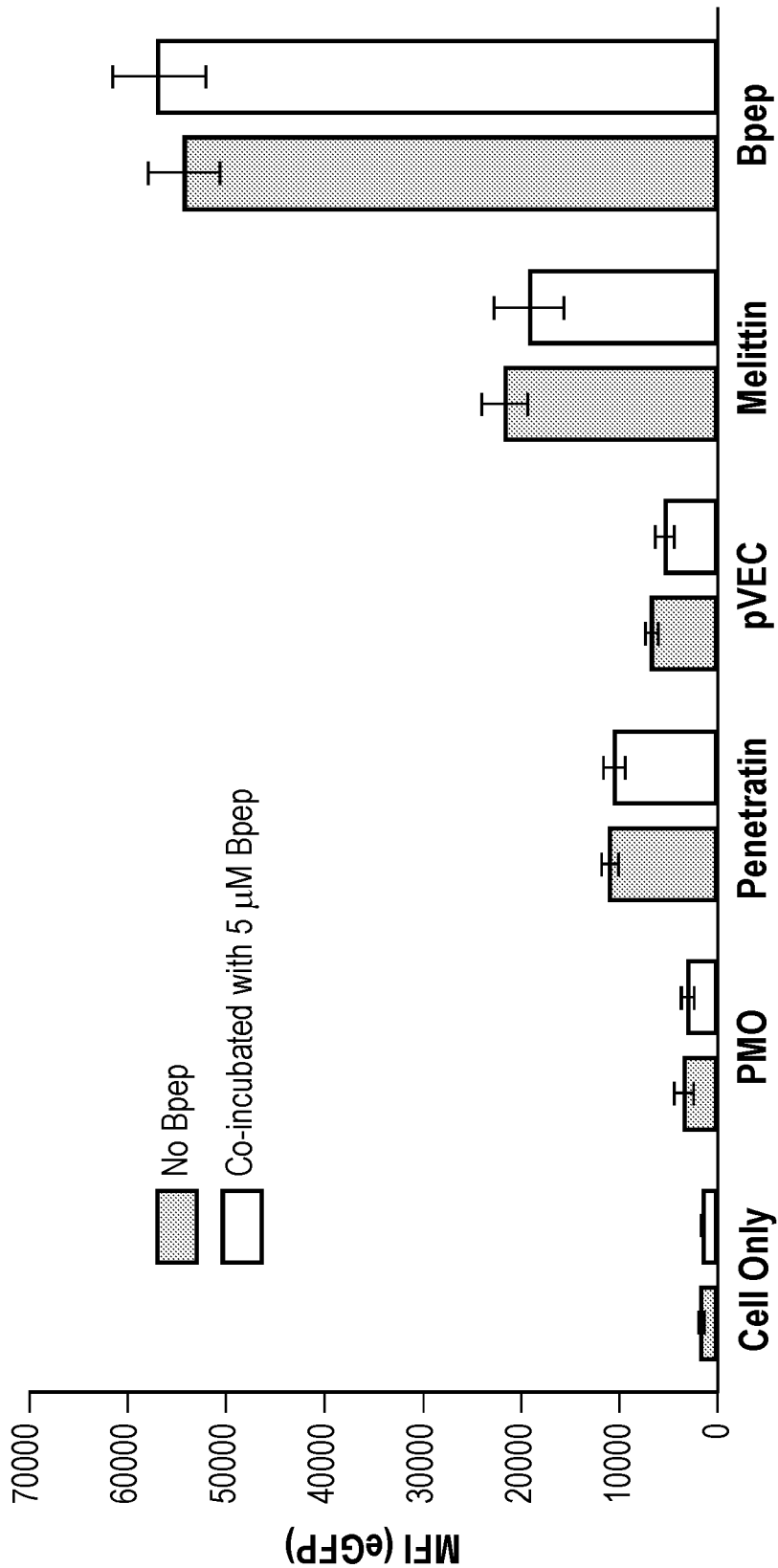

Increase in PMO activity may or may not require the two component peptides of the chimera to be covalently attached. The eGFP assay was repeated with PMO-Penetratin, PMO-pVEC, PMO-Melittin and PMO-Bpep in the presence and absence of 5 μM Bpep (FIG. 2C). In all cases, the PMO-CPP conjugates performed identically in the presence and absence of Bpep. This result demonstrates that covalently linking the two CPPs is necessary to observe an improvement in activity. The eGFP Hela cells provide a functional assay for PMO activity, yet many mechanistic steps contribute to this final read-out. Any of the PMO conjugates must be internalized into cells, escape endosomes if endocytosed, localize to the nucleus, and bind to pre-mRNA to generate any effect. The different parts of the chimera may be aiding in one or many of these steps. While it is challenging to conclusively demonstrate the exact mechanism given the complexity of the biological processes involved, one model chimera was chosen to thoroughly study to gain additional insight. PMO-pVEC-Bpep was chosen for this purpose, since it demonstrated synergy and did not disrupt the plasma membrane. Additionally, the poor performance of PMO-pVEC made the strong performance of PMO-pVEC-Bpep a surprising and intriguing result.

Figures 3A, 3B:
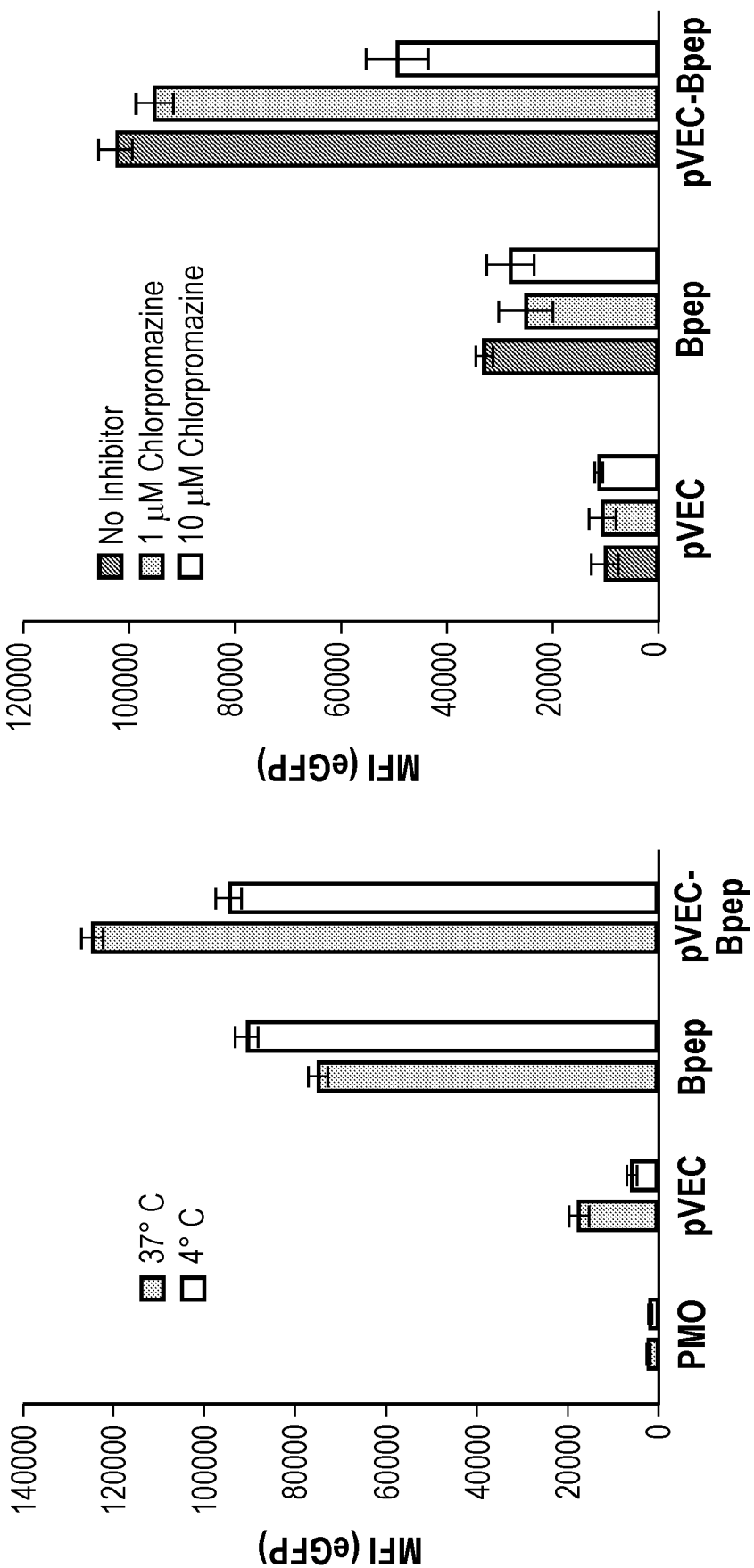
FIG. 3 A) Shows a plot of eGFP mean fluorescence intensity for cells treated at either 37° C. or 4° C.

Mechanistic studies were conducted with experiments to assess cellular uptake pathways. To examine if energy-dependent pathways are involved, PMO activity was measured after treatment at 4° C. vs. 37° C. The experiments were performed in a pulse-chase format in which the HeLa eGFP cells were incubated with 5 M PMO-pVEC, PMO-Bpep, or PMO-pVEC-Bpep for 3 hours at either 4° C. or 37° C. (FIG. 3A). Then, the treatment media was exchanged for fresh media and the cells were allowed to grow for an additional 22 hours. For all compounds except PMO-Bpep, there was a decrease in eGFP fluorescence when treated at 4° C. This result suggests that energy-dependent mechanisms are relevant to the uptake of the PMO-pVEC-Bpep chimera. Of note particularly to the PMO-Bpep results is that any conjugate that binds to the surface of the cells during treatment at 4° C. could be subsequently internalized and trigger eGFP expression when the cells are incubated for an additional 22 hours at 37° C. after treatment. In addition, the effect of multiple endocytosis inhibitors on the internalization of PMO-pVEC, PMO-Bpep, and PMO-pVEC-Bpep into cells was studied (FIG. 3B). The experiments were performed in a pulse-chase format in which the eGFP Hela cells were pre-incubated with the inhibitors. After thirty minutes of pre-incubation, the peptide was added and after three hours, the treatment media was exchanged with fresh media and the cells were left to grow for another 22 hours. The majority of the inhibitors had no effect. However, at high concentrations of chlorpromazine, eGFP fluorescence decreased in the cells treated with the PMO-pVEC-Bpep chimera. While chlorpromazine is considered an inhibitor of clathrin-mediated endocytosis, it may possibly affect downstream components of the process too.

Beyond the possible role of clathrin-mediated endocytosis in the uptake of the chimera, these data demonstrate that the chimera is accessing a unique internalization mechanism since no appreciable decrease was observed with either PMO-pVEC or PMO-Bpep.

Finally, the constructs were labeled with a small molecule organic dye orthogonal to eGFP to allow simultaneous monitoring of the uptake of the compounds and functional exon-skipping activity. Experiments of this format could help deconvolute cellular internalization from PMO efficacy. To prepare these compounds, pVEC, Bpep and pVEC-Bpep were synthesized with a cysteine residue on the N-terminus of the sequence and the terminus was then capped with 4-pentynoic acid as before. After purification by RP-HPLC, the peptides were dissolved in water with equimolar Sulfo-Cyanine5 maleimide and purified again by RP-HPLC. Finally, the SulfoCy5-labeled peptides were all conjugated to the PMO-azide through copper-catalyzed click chemistry and purified by RP-HPLC.

Figure 4A:
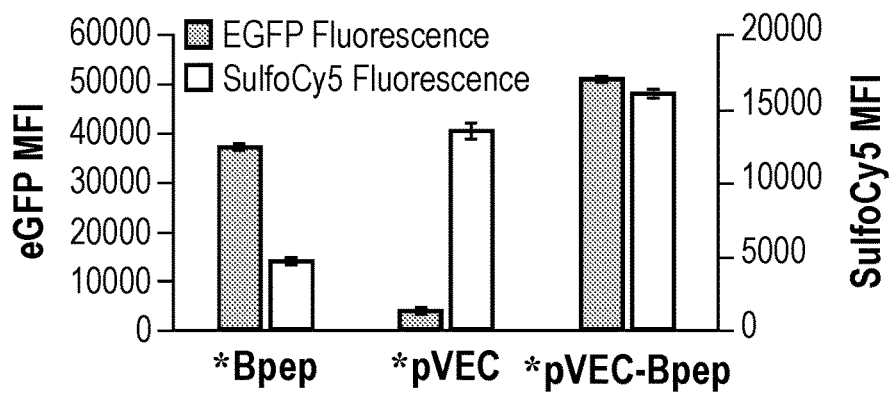
FIG. 4 A) Shows a plot demonstrating the mean fluorescence intensity in each respective channel for eGFP and SulfoCy5 for HeLa 654 cells treated with 5 µM PMO-SulfoCy5-pVEC, PMO-SulfoCy5-Bpep, or PMO-SulfoCy5-pVEC-Bpep for 22 hours at 37° C.

Using the SulfoCy5-labeled constructs, a flow cytometry experiment with the eGFP Hela cells was performed. The cells were treated with 5 μM of each conjugate in serum-containing media for 22 hours and then analyzed by flow cytometry (FIG. 4A). For eGFP fluorescence, the 488 nm excitation laser and 530 nm emission filter were used, and for the SulfoCy5, the 561 nm excitation laser and 695 nm emission filter were used. The separation of channels enabled fluorescence from both fluorophores to be simultaneously recorded. Unlabeled PMO-pVEC, PMO-Bpep, and PMO-pVEC-Bpep was treated to determine if the fluorophore was perturbing the effect of a given conjugate. In all cases, eGFP fluorescence was slightly decreased with the fluorophore attached suggesting that while the fluorophore may affect the efficacy of the conjugate, it does so uniformly.

In terms of SulfoCy5 fluorescence, PMO-SulfoCy5-Bpep exhibited less fluorescence than PMO-SulfoCy5-pVEC or PMO-SulfoCy5-pVEC-Bpep. However, PMO-SulfoCy5-Bpep had a relatively high ability to facilitate eGFP expression. This result suggests that while the overall cellular uptake of PMO-Bpep is less than PMO-pVEC, Bpep has a beneficial downstream effect. Perhaps improved endosomal escape, nuclear entry, RNA binding, or splice-modification results in the relatively high eGFP fluorescence for PMO-Bpep. On the other hand, PMO-SulfoCy5-pVEC had high SulfoCy5 fluorescence, but poor eGFP expression, which indicates that the compound has good cellular uptake but has limitations elsewhere downstream. The pVEC-Bpep chimera exhibited both the highest eGFP expression and the highest SulfoCy5 fluorescence, though the SulfoCy5 fluorescence was on a similar scale to pVEC. Therefore, the hypothesis for the basis of the chimera's synergy is that the pVEC component is improving cellular uptake without interfering with the beneficial downstream effects of Bpep.

To further test this hypothesis and examine to what extent the material localized to endosomes, a live cell confocal microscopy imaging experiments on the HeLa eGFP cells was done. The same treatment conditions as the flow cytometry assay were used except that a Rab5a-RFP fusion protein was used to label early endosomes. After treatment and sixteen hours prior to imaging, the HeLa eGFP cells were transiently transfected with a Rab5a-RFP fusion construct utilizing a baclovirus vector. It was reasoned that if PMO-SulfoCy5-pVEC had poor efficacy in triggering eGFP expression due to endosomal entrapment, the RFP signal would be co-localized with the SulfoCy5 signal.

Figure 4B:
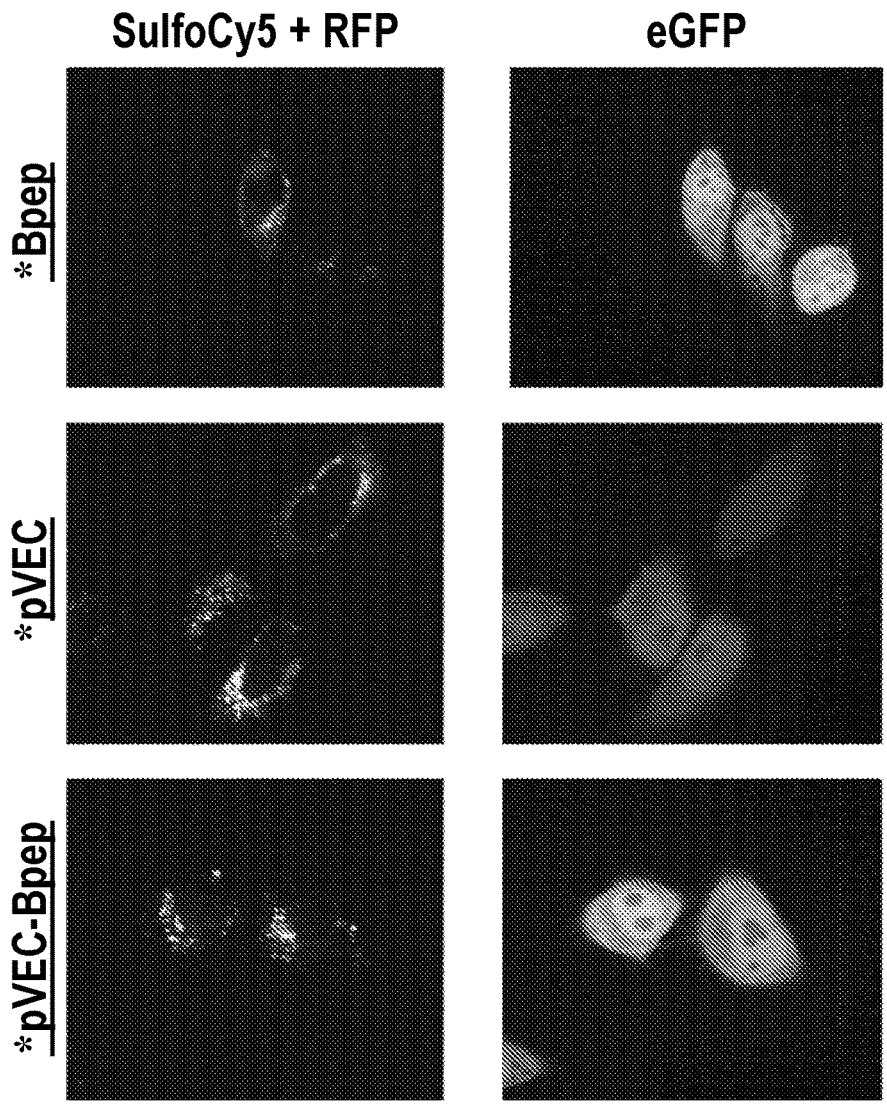

The imaging data correlate very well with the flow cytometry data (FIG. 4B). With both PMO-SulfoCy5-pVEC and PMO-SulfoCy5-pVEC-Bpep, the bright SulfoCy5 signal is concentrated in punctae. Some SulfoCy5 signal is co-localized with RFP signal, demonstrating localization to the early endosome, while other SulfoCy5 punctae are likely late endosomes and lysosomes. These images provide further evidence that the primary mechanism of internalization is endocytosis and that endosomal entrapment can limit PMO activity for certain constructs, despite significant cellular uptake.

Herein it was shown with mechanistic studies that individual CPPs may be helpful with different elements of macromolecule delivery. It was also shown that chimeric peptides composed of CPPs can exhibit synergistic improvements in PMO delivery and exon skipping efficiency. The relative position of the sequences affects the degree of uptake, that both peptides must be CPPs, and that they must be covalently attached to observe the effect.

Example 1: General Method for Peptide Preparation and Purification

Fast-Flow Peptide Synthesis

Peptides were synthesized on a 0.1-mmol scale using an automated flow peptide synthesizer. ChemMatrix Rink Amide HYR resin (200 mg) was loaded into a reactor maintained at 90° C. All reagents were flowed at 80 mL/min with HPLC pumps through a stainless steel loop maintained at 90° C. before introduction into the reactor. For each coupling, 10 mL of a solution containing 0.2 M amino acid and 0.2 M HATU in DMF were mixed with 200 μL diisopropylethylamine and delivered to the reactor. Fmoc removal was accomplished using 10.4 mL of 20% (v/v) piperidine. Between each step, 15 mL of DMF were used to wash out the reactor. The final coupling was with 4-pentynoic acid, rather than an amino acid, but using the same conditions. After completion of the synthesis, the resins were washed 3 times with DCM and dried under vacuum.

Peptide Cleavage and Deprotection

Each peptide was subjected to simultaneous global side-chain deprotection and cleavage from resin by treatment with 6 mL of Reagent K (82.5% trifluoroacetic acid, 5% phenol, 5% water, 5% thioanisole, and 2.5% 1,2-ethanedithiol (EDT)). Cleavages were left at room temperature for 16 hours to ensure complete removal of Pbf. The cleavage cocktail was filtered to remove the resin and was evaporated by bubbling N2 through the mixture. Then ~35 mL of cold ether was added and the crude product was pelleted through centrifugation for three minutes. This ether trituration and centrifugation was repeated two more times. After the third wash, the pellet was redissolved in 50% water and 50% acetonitrile and lyophilized.

Peptide Purification

Solvent A: water containing 0.1% TFA
Solvent B: acetonitrile containing 0.1% TFA Lyophilized peptide was dissolved into a minimum volume of mobile phase (95% A, 5% B). The solution was loaded onto a reversed-phase HPLC column (Agilent Zorbax SB C18 column: 9.4×250 mm, 5 μm or Agilent Zorbax SB C3 column: 9.4×250 mm, 5 μm) attached to a mass-based purification system. A linear gradient was run at 0.5% B/min from 5% B to 55% B. Using mass data about each fraction from the instrument, only pure fractions were pooled and lyophilized. The purity of the fraction pool was confirmed by LC-MS.

Figure 1C:
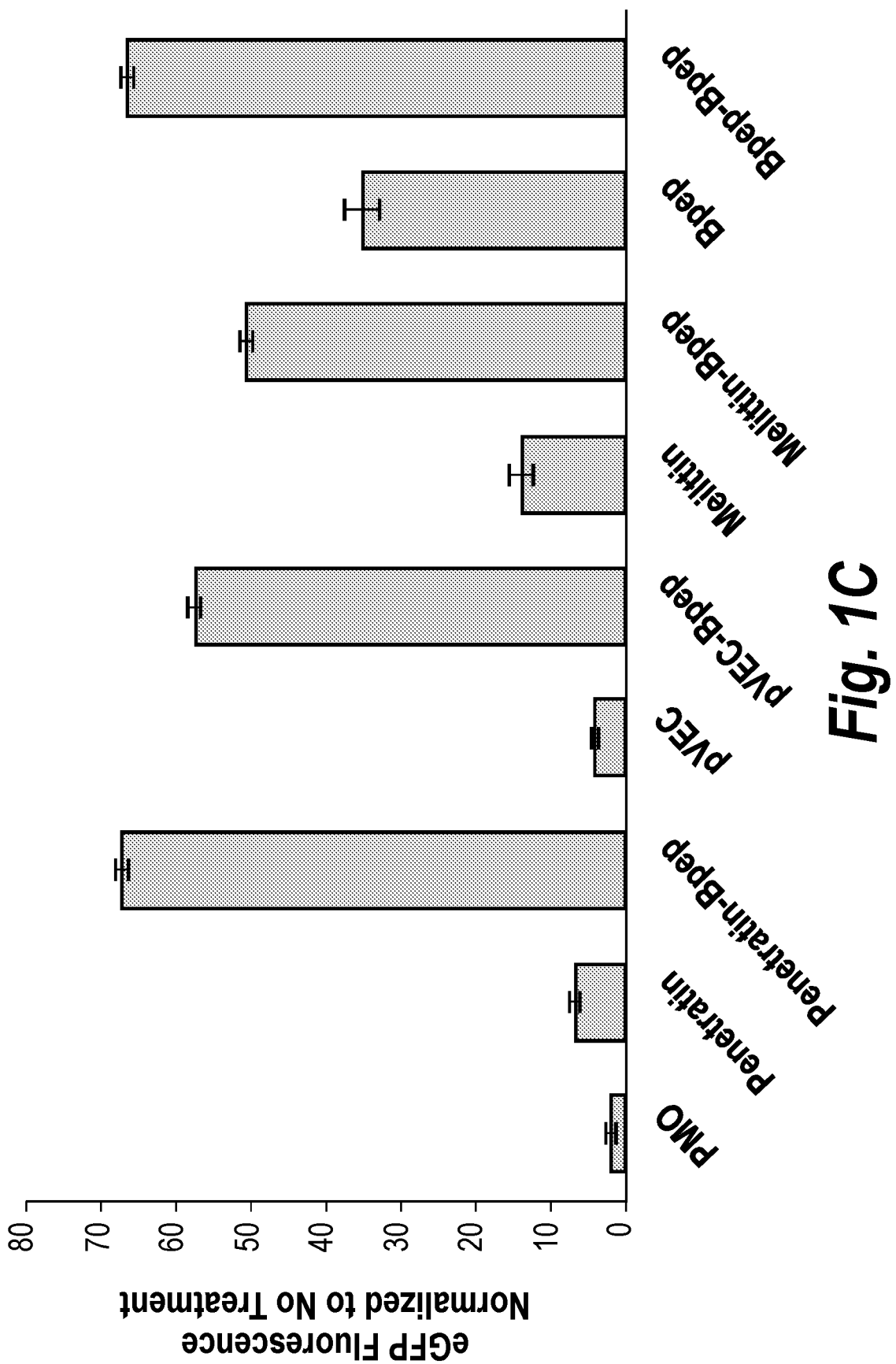

Using the protocol of Example 1, the peptides of FIG. 1A and Table 2 were synthesized.

TABLE 2 cell penetrating peptides

| CPP Name | CPP Class | Amino Acid Sequence* |
|---|---|---|
| Bpep | polyarginine | RXRRBRRXRRBR (SEQ ID NO: 6) |
| Penetratin | Amphipathic | RQIKIWFQNRRMKWKK (SEQ ID NO: 11) |
| pVEC | Amphipathic | LLIILRRRIRKQAHAHSK (SEQ ID NO: 12) |
| Melittin | Cationic | GIGAVLKVLT TGLPALISWI KRKRQQ (SEQ ID NO: 13) |

*X is aminohexanoic acid and B is β-alanine

Example 2: Peptide Conjugation

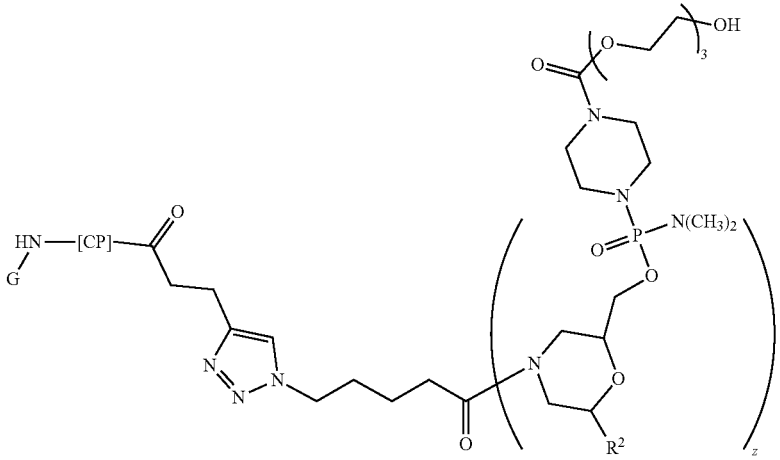

Procedure for Coupling 5-Azidopentanoic to PMO

PMO IVS-654 ($R_2$=5'-GCT ATT ACC TTA ACC CAG-3' (SEQ ID NO: 14); z=18) (200 mg, 32 μmol) was dissolved in 600 μL DMSO. To the solution was added a solution containing 4 equivalents of 5-azidopentanoic acid (13.6 μL, 128 μmol) activated with HBTU (320 μL of 0.4 M HBTU in DMF, 128 μmol) and DIEA (22.3 μL, 128 μmol) in 244 μL DMF (Final reaction volume=1.2 mL). The reaction proceeded for 25 minutes before being quenched with 1 ml of water and 2 mL of ammonium hydroxide. The ammonium hydroxide will hydrolyze any ester formed during the course of the reaction. After 1 hour, the solution was diluted to 40 mL and purified using reversed-phase HPLC (Agilent Zorbax SB C3 column: 21.2×100 mm, 5 μm) and a linear gradient from 2 to 60% B (solvent A: water; solvent B: acetonitrile) over 58 minutes (1% B/min). Using mass data about each fraction from the instrument, only pure fractions were pooled and lyophilized. The purity of the fraction pool was confirmed by LC-MS. Lyophilization afforded 171 mg of dry powder (84% yield).

General Procedure for PMO-Peptide Conjugation by Azide/Alkyne Huisgen Cycloaddition A 20 mL scintillation vial with a septum cap was charged with peptide alkyne (1.1 μmol), ISV2-654 azide (0.95 μmol), and copper bromide (0.05 mmol). The vial was purged with nitrogen for 5 minutes to ensure the removal of oxygen before the addition of ~ 1 mL of DMF through the septum. The reaction mixture was vortexed for 1 minute. After 2 hours, the reaction mixture was diluted with 10 mL of 50 mM Tris (pH 8), and loaded onto reversed-phase HPLC column (Agilent Zorbax SB C3 9.4×50 mm, 5 μm). Chromatography was performed using a linear gradient from 5-45% B over 20 minutes. Solvent A: 5 mM ammonium acetate, pH=8 in water; solvent B: 5 mM ammonium acetate pH=8 in 90% acetonitrile 10% water. Using mass data about each fraction from the instrument, only pure fractions were pooled and lyophilized. The purity of the fraction pool was confirmed by LC-MS.

Example 3: Fluorophore Conjugation

For fluorophore-labeled PMO-peptide conjugates, the organic dye was attached prior to conjugation to PMO. Equimolar SulfoCy5-maleimide was conjugated to cysteine-containing peptides in 1 mL of $H_2O$. After 30 minutes, the reactions were purified by reversed-phase HPLC using a linear gradient from 5-45% B over 80 minutes for pVEC and pVEC-Bpep and a linear gradient from 1-31% B over 60 minutes for Bpep. Mobile phase A: water with 0.1% TFA. Mobile phase B: acetonitrile with 0.1% TFA.

Example 4: Flow Cytometry

In order to test the library of chimeric peptide-oligonucleotide-conjugates, flow cytometry analysis of GFP fluorescence was conducted. HeLa 654 cells were maintained in MEM supplemented with 10% (v/v) fetal bovine serum (FBS) and 1% (v/v) penicillin-streptomycin at 37° C. and 5% $CO_2$. Eighteen hours prior to treatment, the cells were plated at a density of 5,000 cells per well in a 96-well plate in MEM supplemented with 10% FBS and 1% penicillin-streptomycin. The day of the experiment, stocks of each PMO-peptide conjugate were prepared in phosphate-buffered serum (PBS). The concentration of the stocks was determined by measuring the absorbance at 260 nm and using an extinction coefficient of 168,700 L $mol^{-1}$ $cm^{-1}$. Cells were incubated with each respective conjugate at a concentration of 5 μM in MEM supplemented with 10% FBS and 1% penicillin-streptomycin for 22 hours at 37° C. and 5% $CO_2$. Next, the treatment media was aspirated the cells were incubated with Trypsin-EDTA 0.25% for 15 min at 37° C. and 5% $CO_2$, washed 1× with PBS, and resuspended in PBS with 2% FBS and 2 μg/mL propidium iodide. Flow cytometry analysis was carried out on a BD LSRII flow cytometer. Gates were applied to the data to ensure that cells that were highly positive for propidium iodide or had forward/side scatter readings that were sufficiently different from the main cell population were excluded. Each histogram contains at least 3,000 gated events, with the exception of cells treated with PMO-Melittin-Bpep.

Results are shown in FIG. 1C, 2A, 2B, 2C, and Table 3.

TABLE 3 chimeric peptide-oligonucleotide-conjugates compared to unconjugated PMO and single CPP-PMO conjugate.

| Chimeric Peptide | Activity Relative to PMO | Single CPP | Activity of Chimeric Peptide to Single Peptide |
|---|---|---|---|
| Penetratin-Bpep | 67 | Penetratin | 8 |
| pVEC-Bpep | 59 | pVEC | 10 |
| Melitin-Bpep | 55 | Melitin | 4 |
| Bpep-Bpep | 70 | Bpep | 2 |

Example 5: Inhibitor Experiments

To inhibit a variety of endocytic mechanisms, a pulse-chase experiment was performed. Briefly, HeLa 654 cells were plated at a density of 5,000 cells per well in a 96-well plate in MEM supplemented with 10% FBS and 1% penicillin-streptomycin. The next day, the cells were treated with each inhibitor at the indicated concentration. After 30 minutes, PMO-peptide conjugate was added to each well at a concentration of 5 μM. After incubation at 37° C. and 5% $CO_2$ for 3 hours, the treatment media was replaced with fresh media (no inhibitor or PMO-peptide) and the cells were allowed to grow for another 22 hours at 37° C. and 5% $CO_2$. For the 4° C. experiments, the day after plating, the cells were pre-incubated for 30 minutes at 4° C., followed by the addition of PMO-peptide conjugate to each well at a concentration of 5 μM. After incubation at 4° C. for 3 hours, the treatment media was replaced with fresh media and the cells were allowed to grow for another 22 hours at 37° C. and 5% $CO_2$. Sample preparation and flow cytometry was then performed as described above. Each histogram contains at least 3,000 gated events, with the exception of treatment with 20 μM cytochalasin D.

Results are shown in FIGS. 3A and 3B.

Example 6: Live-Cell Confocal Imaging

HeLa 654 cells were plated at a density of 5,000 cells per well in a #1.5 coverslip glass-bottom 96-well plate in MEM supplemented with 10% FBS and 1% penicillin-streptomycin. Twenty-four hours later, PMO-SulfoCy5-peptide conjugate was added to each well at a concentration of 5 μM. Six hours after that (eighteen hours prior to imaging), 3 μL of CellLight™ Early Endosomes-RFP, BacMam 2.0 was added to each well (corresponding to 30 particles per cell). To prepare for imaging, the treatment media was aspirated, the cells were washed twice with PBS, the cells were stained for 10 minutes with 2 μg/mL Hoescht in PBS followed by two more PBS washes. Finally, the cells were imaged in PBS on an RPI spinning disk confocal microscope.

Results are shown in FIGS. 4A and 4B.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A chimeric peptide-oligonucleotide conjugate of Formula I:

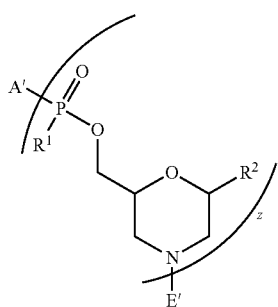

(I)

or a pharmaceutically acceptable salt thereof,
wherein:

A' is selected from —NHCH$_2$C(O) NH$_2$, —N(C$_{1-6}$-alkyl) CH$_2$C(O) NH$_2$,

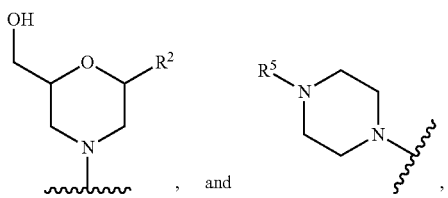

and wherein

R$^5$ is —C(O)(O-alkyl)$_x$-OH, wherein x is 3-10 and each alkyl group is, independently at each occurrence, C$_{2-6}$-alkyl, or R$^5$ is selected from —C(O)C$_{1-6}$-alkyl, trityl, monomethoxytrityl, —(C$_{1-6}$-alkyl)-R$^6$, —(C$_{1-6}$-heteroalkyl)-R$^6$, aryl-R$^6$, heteroaryl-R$^6$, —C(O)O—(C$_{1-6}$-alkyl)-R$^6$, —C(O)O-aryl-R$^6$, —C(O)O— heteroaryl-R$^6$, and

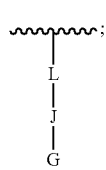

;

wherein R$^6$ is selected from OH, SH, and NH$_2$, or R$^6$ is O, S, or NH, each of which are covalently-linked to a solid support;

each R$^1$ is independently selected from OH and —N(R$^3$)(R$^4$), wherein each R$^3$ and R$^4$ are, independently at each occurrence, —C$_{1-6}$-alkyl;

each R$_2$ is independently selected from H, a nucleobase, and a nucleobase functionalized with a chemical protecting-group, wherein the nucleobase, independently at each occurrence, comprises a C$_{3-6}$-heterocyclic ring selected from pyridine, pyrimidine, triazinane, purine, and deaza-purine;

z is 8-40; and

E' is selected from H, —C$_{1-6}$-alkyl, —C(O)C$_{1-6}$-alkyl, benzoyl, stearoyl, trityl, monomethoxytrityl, dimethoxytrityl, trimethoxytrityl,

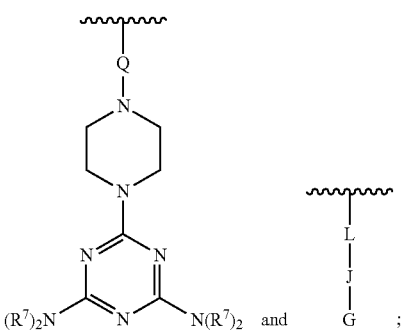

wherein

Q is —C(O)(CH$_2$)$_6$C(O)— or —C(O)(CH$_2$)$_2$S$_2$(CH$_2$)$_2$C(O)—;

R$^7$ is —(CH$_2$)$_2$OC(O)N(R$^8$)$_2$, wherein R$^8$ is —(CH$_2$)$_6$NHC(=NH)NH$_2$;

L is —C(O)(CH$_2$)$_{1-6}$—C$_{1-6}$-heteroaromatic-(CH$_2$)$_{1-6}$C(O)—, wherein L is covalently-linked by an amide bond to the amino-terminus of J;

J is 2, 3, 4, or 5 covalently-linked cell-penetrating peptides;

G is selected from H, —C(O)C$_{1-6}$-alkyl, benzoyl, and stearoyl, wherein G is covalently-linked by an amide bond to the carboxy-terminus of J;

wherein at least one of the following conditions is true:

1) A' is 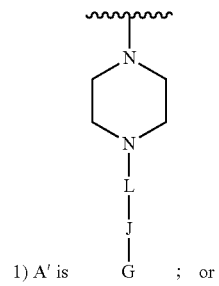 ; or

2) E' is 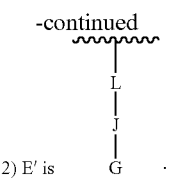.

wherein at least one of the cell-penetrating peptides is an amphipathic peptide and at least one of the cell-penetrating peptides is an oligoarginine peptide; and
further wherein the oligoarginine peptide comprises the sequence [(RY$_z$R)$_x$] (SEQ ID NOs: 15-18), wherein R is arginine, Y is independently selected from aminohexanoic acid (X) or β-alanine (B), z is 1, and x is 1, 2, 3, 4, or 5.

2. The chimeric peptide-oligonucleotide conjugate of claim 1, or a pharmaceutically acceptable salt thereof, wherein J is 2 covalently-linked cell-penetrating peptides.

3. The chimeric peptide-oligonucleotide conjugate of claim 1, or a pharmaceutically acceptable salt thereof, wherein the oligoarginine peptide comprises the sequence [(RXR)(RBR)]$_x$ (SEQ ID NOs: 8 and 10) or [(RBR)(RXR)]$_x$ (SEQ ID NOs: 7 and 9), wherein R is arginine, X is aminohexanoic acid, B is β-alanine, and x is 1 or 2.

4. The chimeric peptide-oligonucleotide conjugate of claim 1, or a pharmaceutically acceptable salt thereof, wherein the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, and tryptophan, and wherein the hydrophilic peptidyl segment comprises a sequence of 2-20 amino acids independently selected from charged amino acids, polar uncharged amino acids, or hydrophobic amino acids, wherein the hydrophilic peptidyl segment comprises at least one non-hydrophobic amino acid.

5. The chimeric peptide-oligonucleotide conjugate of claim 1, or a pharmaceutically acceptable salt thereof, wherein J is penetratin-Bpep

```
                                          (SEQ ID NO: 1)
(RQIKIWFQNR RMKWKKRXRR BRRXRRBR), pVEC-Bpep
                                          (SEQ ID NO: 2)
(LLIILRRRIR KQAHAHSKRX RRBRRXRRBR), or melittin-Bpep
                                          (SEQ ID NO: 3)
(GIGAVLKVLT TGLPALISWI KRKRQQRXRR BRRXRRBR).
```

6. The chimeric peptide-oligonucleotide conjugate of claim 1, or a pharmaceutically acceptable salt thereof, wherein E' is selected from H, —C$_{1-6}$-alkyl, —C(O)C$_{1-6}$-alkyl, benzoyl, stearoyl, trityl, monomethoxytrityl, dimethoxytrityl, trimethoxytrityl, and

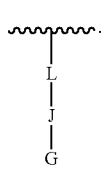

7. The chimeric peptide-oligonucleotide conjugate of claim 1, or a pharmaceutically acceptable salt thereof, wherein
A' is selected from —N(C$_{1-6}$-alkyl)CH$_2$C(O)NH$_2$,

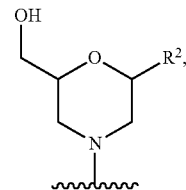

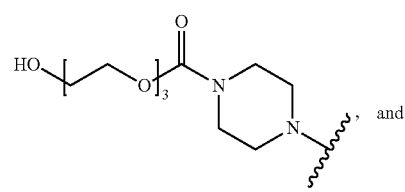, and

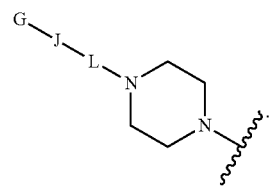

8. The chimeric peptide-oligonucleotide conjugate of claim 1, or a pharmaceutically acceptable salt thereof, wherein A' is selected from —N(C$_{1-6}$-alkyl)CH$_2$C(O)NH$_2$,

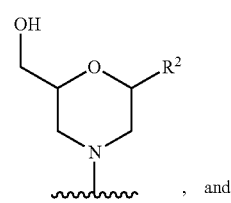, and

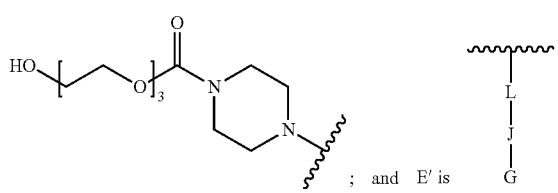

9. The chimeric peptide-oligonucleotide conjugate of claim 1, or a pharmaceutically acceptable salt thereof, wherein the peptide-oligonucleotide conjugate of Formula I is a peptide-oligonucleotide conjugate selected from:

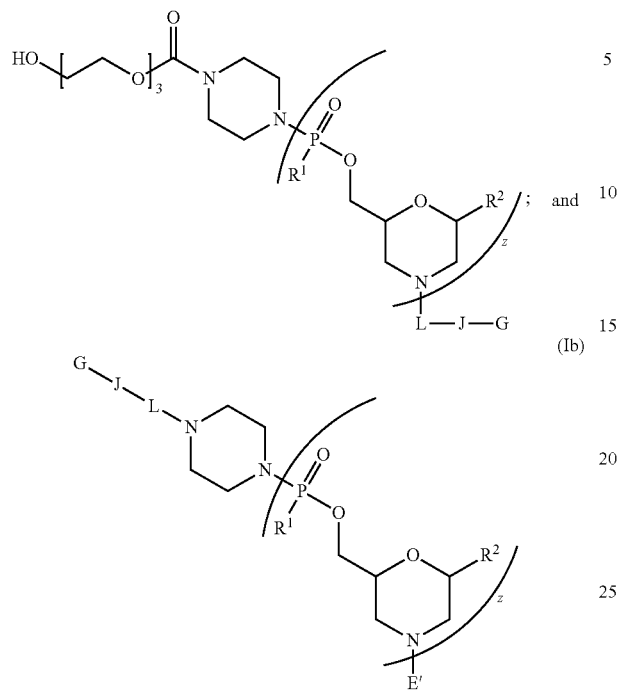

(Ia)

(Ib)

wherein E' is selected from H, C$_{1-6}$-alkyl, —C(O)CH$_3$, benzoyl, and stearoyl.

10. The chimeric peptide-oligonucleotide conjugate of claim 9, or a pharmaceutically acceptable salt thereof, wherein the peptide-oligonucleotide conjugate is of the Formula (Ia).

11. The chimeric peptide-oligonucleotide conjugate of claim 1, or a pharmaceutically acceptable salt thereof, wherein each R$^1$ is N(CH$_3$)$_2$.

12. The chimeric peptide-oligonucleotide conjugate of claim 1, or a pharmaceutically acceptable salt thereof, wherein each R$_2$ is a nucleobase, independently at each occurrence, selected from adenine, guanine, cytosine, 5-methyl-cytosine, thymine, uracil, and hypoxanthine.

13. The chimeric peptide-oligonucleotide conjugate of claim 1, or a pharmaceutically acceptable salt thereof, wherein L is —C(O)(CH$_2$)$_{1-6}$-triazole-(CH$_2$)$_{1-6}$C(O)—.

14. The chimeric peptide-oligonucleotide conjugate of claim 1, or a pharmaceutically acceptable salt thereof, wherein L is

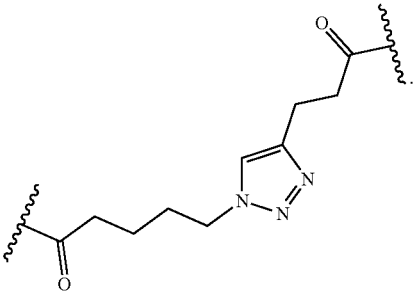 [SMILES: *C(=O)CCCCn1cc(CCC(*)=O)nn1]

15. The chimeric peptide-oligonucleotide conjugate of claim 1, or a pharmaceutically acceptable salt thereof, wherein G is selected from H, C(O)CH$_3$, benzoyl, and stearoyl.

16. A chimeric composition comprising a chimeric peptide-oligonucleotide conjugate of claim 1, or a pharmaceutically acceptable salt thereof, and at least one pharmaceutically acceptable carrier.

17. A method of treating a neuromuscular disease in a subject in need thereof, the method comprising administering a therapeutically effective amount of the chimeric peptide-oligonucleotide conjugate of claim 1, or a pharmaceutically acceptable salt thereof, to the subject.

18. The method of claim 17, where the neuromuscular disease is Duchenne muscular dystrophy.

19. The chimeric peptide-oligonucleotide conjugate of claim 1, or a pharmaceutically acceptable salt thereof, wherein J is two covalently-linked cell-penetrating peptides, and wherein the oligoarginine peptide is the C-terminus of J and the amphipathic peptide is the N-terminus of J.

* * * * *